(12) United States Patent
Amobi et al.

(10) Patent No.: US 8,927,579 B2
(45) Date of Patent: Jan. 6, 2015

(54) MALE CONTRACEPTIVE

(75) Inventors: Nnae-Meka Ikechukwu Amobi, London (GB); Christopher Smith, London (GB)

(73) Assignees: Nnaemkea Ikechukwu Amobi, London (GB); Ian Christopher Smith, London (GB)

( * ) Notice: Subject to any disclaimer, the term of this patent is extended or adjusted under 35 U.S.C. 154(b) by 1035 days.

(21) Appl. No.: 12/504,287

(22) Filed: Jul. 16, 2009

(65) Prior Publication Data
US 2010/0029624 A1 Feb. 4, 2010

Related U.S. Application Data

(63) Continuation of application No. PCT/GB2008/000163, filed on Jan. 17, 2008.

(30) Foreign Application Priority Data

Jan. 17, 2007 (GB) .................................. 0700893.1

(51) Int. Cl.
| | |
|---|---|
| A01N 43/00 | (2006.01) |
| A61K 31/445 | (2006.01) |
| A01N 43/64 | (2006.01) |
| A61K 31/41 | (2006.01) |
| A01N 31/14 | (2006.01) |
| A61K 31/075 | (2006.01) |
| A01N 33/18 | (2006.01) |
| A01N 33/24 | (2006.01) |
| A61K 31/04 | (2006.01) |
| C07C 211/27 | (2006.01) |
| C07C 211/45 | (2006.01) |
| C07C 217/16 | (2006.01) |
| C07D 207/09 | (2006.01) |
| C07D 209/08 | (2006.01) |
| C07D 211/12 | (2006.01) |
| C07D 211/14 | (2006.01) |
| C07D 211/26 | (2006.01) |
| C07D 215/06 | (2006.01) |
| C07D 215/12 | (2006.01) |
| C07D 217/10 | (2006.01) |
| C07D 221/04 | (2006.01) |
| C07D 279/26 | (2006.01) |
| C07D 279/28 | (2006.01) |
| C07D 295/03 | (2006.01) |
| C07D 401/06 | (2006.01) |
| C07D 417/06 | (2006.01) |

(52) U.S. Cl.
CPC ............ *C07C 211/27* (2013.01); *C07C 211/45* (2013.01); *C07C 217/16* (2013.01); *C07D 207/09* (2013.01); *C07D 209/08* (2013.01); *C07D 211/12* (2013.01); *C07D 211/14* (2013.01); *C07D 211/26* (2013.01); *C07D 215/06* (2013.01); *C07D 215/12* (2013.01); *C07D 217/10* (2013.01); *C07D 221/04* (2013.01); *C07D 279/26* (2013.01); *C07D 279/28* (2013.01); *C07D 295/03* (2013.01); *C07D 401/06* (2013.01); *C07D 417/06* (2013.01); *C07C 2103/26* (2013.01)
USPC ........... 514/315; 514/317; 514/331; 514/359; 514/715; 514/716; 514/717; 514/741

(58) Field of Classification Search
USPC .......... 514/315, 317, 331, 359, 715–717, 741
See application file for complete search history.

(56) References Cited

U.S. PATENT DOCUMENTS 2,769,812 A 11/1956 Ruddy

FOREIGN PATENT DOCUMENTS

| GB | 784892 | 10/1957 |
|---|---|---|
| GB | 823733 | 11/1959 |
| WO | 2005021523 | 10/2005 |
| WO | 2005097779 | 10/2005 |
| WO | 2008087421 | 7/2008 |

OTHER PUBLICATIONS

J. G. Cannon, "Analog Design", Chapter Nineteen in Burger's Medicinal Chemistry and Drug Discovery, Fifth Edition, vol. I: Principles and Practice, Wiley-Interscience 1995, pp. 783-802, 784.*

(Continued)

*Primary Examiner* — Kendra D Carter
(74) *Attorney, Agent, or Firm* — Banner & Witcoff, Ltd.

(57) ABSTRACT

A compound having formula I. $R_1$, $R_2$, $R_3$ and $R_4$ are independently H or lower alkyl. $R_5$ is aryl, heteroaryl, cycloalkyl, heterocycloalkyl, aryloxy, heteroaryloxy, cycloalkyloxy, heterocycloalkyloxy, arylamino, heteroarylamino, cycloalkylamino, heterocycloalkyl amino, arylthio, heteroarylthio, cycloalkylthio, heterocycloalkylthio, or cyclic olefin, any of which may be substituted or non-substituted; or substituted alkyl, substituted alkyl oxy or substituted alkyl amino wherein the substituent is an aryl, a heteroaryl, a cycloalkyl, a heterocycloalkyl or a cyclic olefin, any of which may be substituted or non-substituted. X is C or N. n and p are independently whole numbers selected from 0, 1 and 2. $(CH_2)_n$ and $(CH_2)_p$ may be substituted or non-substituted. $Ar_1$ and $Ar_2$ are independently aryl or heteroaryl groups which may be substituted or non-substituted. Certain specific compounds are excluded.

Figure 1A:
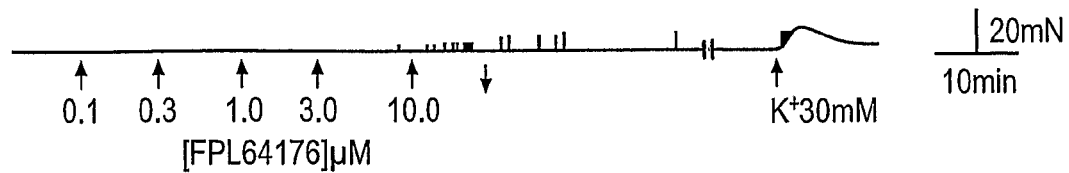

The compounds can be used in a medicament or a method for the reduction or prevention of the emission of sperm, or for the reduction or prevention of transmission of viral agents transmitted in seminal fluid.

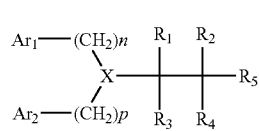

I

8 Claims, 10 Drawing Sheets

(56) References Cited

OTHER PUBLICATIONS

R.P.Sheridan, "The Most Common Chemical Replacements in Drug-Like Compounds" J. Chem.Inf.Comput, Sci., 2002, vol. 42, pp. 103-108.*
Kihlstrom et al. "Some effects of vasopressin of sexual behaviour and seminal characteristics in intact and castrated rabbits" J. Endocr., 1974, vol. 60, pp. 445-453.*
R.E.J. Dyball "The Effects of Drugs on the Release of Vasopressin" Br. J. Pharmac. Chemother, 1968, vol. 33, 329-341.*
Stief et al. "The rabbit as a model for neurourologic studies of the lower genitourinary tract" Word J Urol, 1990, vol. 8, pp. 233-236.*
Seed et al. "Methods for assessing sperm motility, morphology, and counts in the rat, rabbit, and dog: a consensus report" Reproductive Toxicology, 1996, vol. 10, No. 3, pp. 237-244.*
PCT International Search Report.
Bourquin et al., "Neue Phenohtiaziderivate" Helvetica Chimica Acta, Chverlag Helvetical Chimica Acta, Jan. 1, 1959, vol. 42, No. 22-23, pp. 259-281(a Letter also enclosed with a short translation).
PCT International Search Report, Jun. 15, 2009.
Walden et al., "Long-term non-hormonal male contraception in mice using N-butyldeoxynojirimycin," Human Reproduction, 2005.
Van der Spoel et al., Reversible infertility in male mice after oral administration of alkylated imino sugars: A nonhormonal approach to male contraception, PNAS, Dec. 24, 2002, vol. 99, No. 26, pp. 17173-17178.
Amory et al., "Miglustat has no apparent effect on spermatogenesis in normal men," Human Reproduction, 2006.
Khan et al., "Ductus Deferens-a Comparative Histology in Mammals," J. Anat. Soc. India 52(2) 163-165 (2003).
Gupta et al., "Antispermatogenic, antiandrogenic activities of Albizia lebbeck (L.) Benth bark extract in male albino rats," Phytomedicine, 2006, 13(4):277-83.
Kavlock et al., "Mode of action: reduction of testosterone availability—molinate-induced inhibition of spermatogenesis," Crit Rev Toxicol, 2005, 35(8-9):685-90.
Van Der Spoel et al., "Reversible infertility in male mice after oral administration of alkylated imino sugars: a nonhormonal approach to male contraception," Proc Natl Acad Sci, 2002, 24;99(26):17173-8.
Chapin et al., "Methods for assessing rat sperm motility," Reprod Toxicol., 1992, 6(3):267-73.
Ahmad et al., "Regulation of human sperm motility and hyperactivation components by calcium, calmodulin, and protein phosphatases," Arch Androl., 1995, 35(3):187-208.
Carrera et al., "Regulation of protein tyrosine phosphorylation in human sperm by a calcium/calmodulin-dependent mechanism: identification of A kinase anchor proteins as major substrates for tyrosine phosphorylation," Dev Biol., 1996, 180(1):284-96.
Marin-Briggiler et al., "Evidence of the presence of calcium/calmodulin-dependent protein kinase IV in human sperm and its involvement in motility regulation," J Cell Sci, 2005, 118(Pt 9):2013-22.
Schlingmann et al., "Calmodulin and CaMKII in the sperm principal piece: evidence for a motility-related calcium/calmodulin pathway," J Androl., 2007, 28(5):706-16.

* cited by examiner

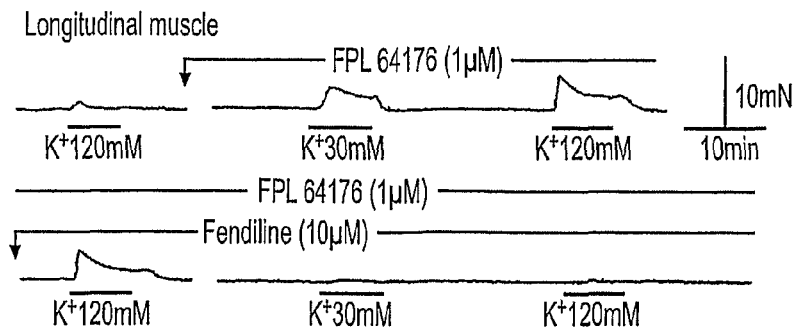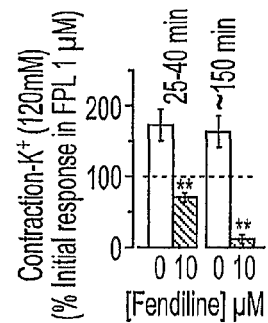
FIG. 3A  FIG. 3B
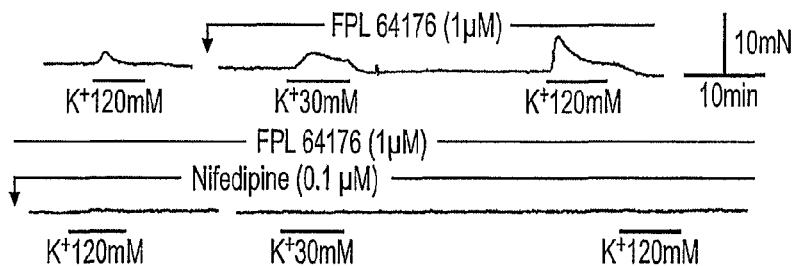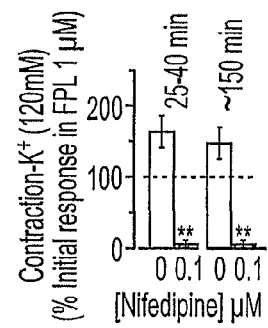
FIG. 3C  FIG. 3D
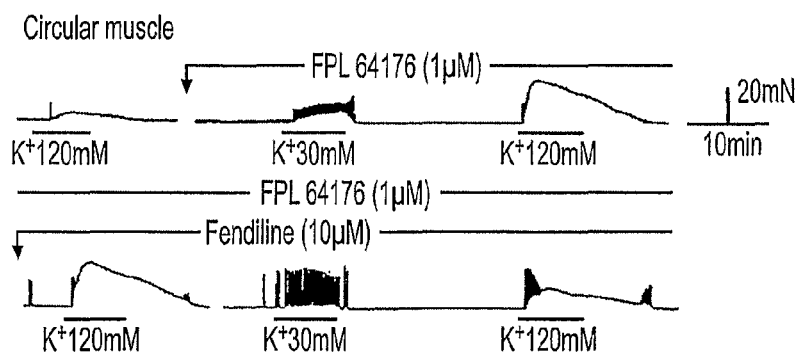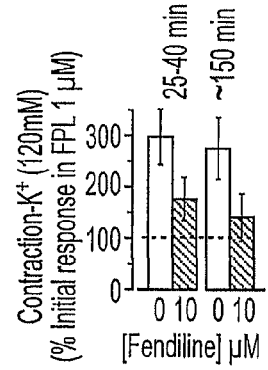
FIG. 4A  FIG. 4B
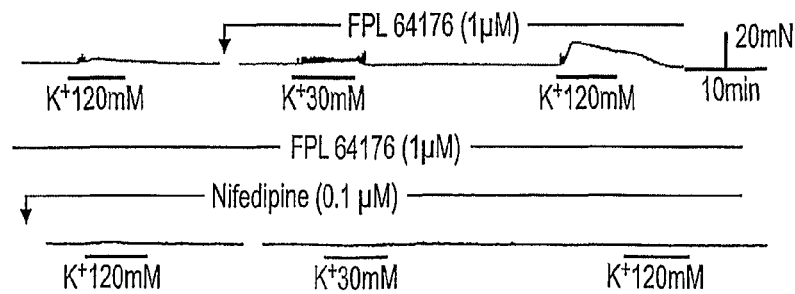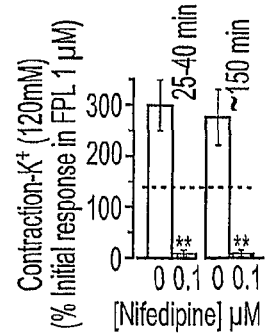
FIG. 4C  FIG. 4D

FENDILINE

PRENYLAMINE

THIORIDAZINE

KHL-8430

MALE CONTRACEPTIVE

The invention relates to new compounds and compositions useful in the regulation of male fertility, especially male contraception.

At present, there are limited male contraceptive options, vasectomy, condoms, self-denial and retraction. Previous research efforts centred on hormonal agents that suppress spermatogenesis have led to the development of testosterone-based preparations, antagonists of gonadotrophin-releasing hormone (GnRH) and progestins. However, these exhibit drawbacks that limit patient compliance. Hormonal-based preparations require intramuscular (weekly/fortnightly) injections with the onset of azoospermia/oligozoospermia being two to three months and reversal three to four months. GnRH-based preparations are peptides and thus also require subcutaneous injections, have short half-lives with azoospermia occurring after six to ten weeks and up to seventeen weeks for reversal. Oral preparations, to be taken two to four times a day have been developed but also exhibit a similar delay in the onset of contraceptive efficacy in addition to other drawbacks such as weight gain, reduction in HDL-cholesterol and ethnic differences in efficacy [15-18, 60]. Research towards the development of non-hormonal methods includes immuno-contraceptive vaccines or agents that alter substrate metabolism and cause sperm deformities or affect sperm maturation and motility [1, 28, 35, 36, 43, 78, 89, 90, 116, 119]. However, these approaches are also sperm-centred and exhibit considerable lag-time to contraceptive efficacy/reversibility.

Whilst research in these areas need to continue in order to overcome the above limitations, there is also a clear need to consider alternative targets involving the control of sperm transport and emission. Research and development of vasocclusive plugs/devices aims to meet this need and recognises the central role of the vas deferens in sperm emission. However, the availability and effective use of vas-plugs and sperm-centred methods in developing countries are hampered by cultural beliefs and lack of qualified personnel. An alternative and perhaps more acceptable approach is the use of drugs to reversibly suppress vas deferens contractility and inhibit sperm transport and emission [22, 73].

Clinical observations and studies indicate that the contractile role of the vas deferens in sperm transport can be controlled through pharmacological intervention. There are consistent reports that two drugs with different therapeutic profiles, notably thioridazine (melleril) or phenoxybenzamine (PBZ, dibenzyline) produce a common and specific side effect, namely the inhibition of sperm emission in hitherto fecund patients [22, 47, 55, 95, 102]. Thioridazine is a piperidine phenothiazine that is used in prophylactic treatment of schizophrenia. PBZ is a β-haloalkyamine irreversible $\alpha_1$-adrenoceptor antagonist that was developed as an antihypertensive drug and for a time, was the drug of choice for the symptomatic treatment of benign prostatic hyperplasia but is now used mainly for pheochromocytoma and vasospasm associated with Raynaud's phenomenon. Well documented double-blind and clinical studies confirmed the putative contraceptive action of thioridazine and reported that it produced this effect within 24 hours of drug administration even at sub therapeutic doses [22, 50, 61, 96]. In separate clinical studies of PBZ, the drug was also found to reversibly inhibit sperm emission in patients. Remarkably, this occurred without effects on libido, penile erection, orgasmic sensation and more importantly blood pressure or hormonal balance [53]. These findings preclude the central or peripheral nervous system as the site of drug action. Furthermore, the studies found no evidence of retrograde ejaculation, indicating that the drug-induced inhibition of sperm emission involves a localised action that disrupts the propulsive function of the vas deferens in sperm transport [56, 84, 97]. Although the mode of drug action underlying this has hitherto remained unclear, the contraceptive actions of thioridazine and PBZ have been exploited clinically.

Thioridazine and PBZ have been used successfully to treat distressing nocturnal emission or premature ejaculation and PBZ proposed and used as an effective male contraceptive [30, 53, 99, 101]. Both drugs are unsuitable for routine use as male contraceptives and it has been surprisingly found that their therapeutic counterparts such as trifluoperazine or prazosin lack the contraceptive side-effect [22, 38, 55, 84]. It would be advantageous to understand how thioridazine and PBZ produce the side effect and then to design new contraceptive drugs utilising this effect. The inventors have studied the in vitro effects of the putative contraceptive drugs and their pharmacological counterparts on the contractility of vasectomy specimens [1-14] and have discovered how the function of the vas deferens is modified in a specific and unique manner by the drugs (thioridazine and PBZ) to produce the contraceptive effect. Using this knowledge the inventors have tested known compounds that are unrelated to thioridazine and PBZ and found that they are able to replicate the contraceptive effects and have also designed new compounds.

Effective functioning of human vas deferens relies on an ordered contraction of its longitudinal and circular muscle layers: longitudinal muscle contraction provides tautness by reducing local transmural slack whilst the co-ordinated rhythmic contractions of both muscle types provide the peristaltic propulsion for efficient sperm transport along its length (~45 cm) and ensures sperm emission [5, 20]. The inventors' in vitro studies (using luminal pressure measurements in uncut human vas deferens, strips of longitudinal muscle and rings of circular muscle) discovered that contractions evoked in the muscle types by different excitatory agents exhibited a clear differential sensitivity to thioridazine, PBZ or fendiline and related drugs but not their pharmacological counterparts. The drugs reliably inhibited longitudinal but not circular muscle contraction, thereby inhibiting its sperm transport function. In vivo, this mode of action disrupts the ordered contractility of both muscle types which sustain efficient propulsive function of the vas deferens. The dual effect of longitudinal muscle inactivation (persistent tissue slack) and the now unabated contraction of circular muscle (lumen closure) prevents sperm transport and inhibits its emission.

The inventors have surprisingly identified the mechanism by which PBZ and thioridazine bring about the contraceptive effects. It was previously thought that the inhibition of sperm emission was brought about by blockade of the alpha-1 adrenoreceptors, but other antagonists of these receptors did not replicate the effects of PBZ and thioridazine. Blocking of calcium channels was also considered [46, 103], calcium influx being required for smooth muscle contraction. However, conventional L-type calcium antagonists also do not produce the contraceptive effect [3, 41]. Without being bound by this theory, the inventors believe that the active agents affect the interaction of calcium-calmodulin ($Ca^{2+}$/CaM) with enzymes other than myosin light chain kinase (MLCK) that modulate muscle contraction. The relative importance and role of various $Ca^{2+}$/CaM-dependent enzyme cascades varies in different smooth muscles and their activation can impart muscle-type specific modulation of contractility via effects on membrane ion channels such as L-type voltage operated Ca$^{2+}$ channels (L-type VOCs), Ca$^{2+}$-dependent K$^+$ and Cl$^-$ channels, and intracellular Ca$^{2+}$ release/re-sequestration mechanisms.

Thioridazine or phenoxybenzamine share a number of pharmacological actions including the blockade of L-type VOCs, of α1-adrenoceptors and activity as calmodulin (CaM) antagonists [29, 74, 75, 83, 122, 128]. However, the pharmacological basis for their differential action in human vas deferens: inhibition of longitudinal compared to circular muscle contractions [2, 4, 9, 11] has remained unclear because it is not replicated by (1-adrenoceptor antagonists [9, 10] or by more traditional L-type Ca$^{2+}$ antagonists [2, 3]. However, the inventors' studies with diphenylalkylamines, found that fendiline and prenylamine but not cinnarizine or flunarizine also produced a differential inhibition of longitudinal muscle contractions [13]. Earlier work by Zimmer and Hofman [130, 131] reported that fendiline and prenylamine but not other diphenylalkylamines belong to a group of drugs that act as more potent antagonists of CaM-dependent enzymes than of MLCK.

Based on their studies, the inventors were able to design new compounds that will act in the same way as the known compounds and bring about the contraceptive effect. According to the invention, there is provided a compound having formula I

Figure 9:
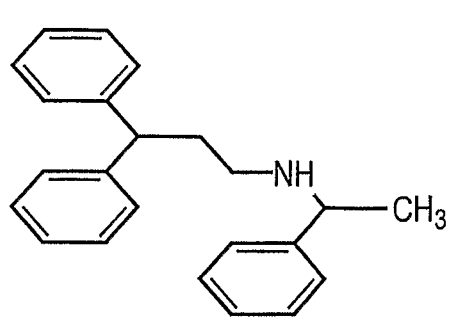
Figure 9:
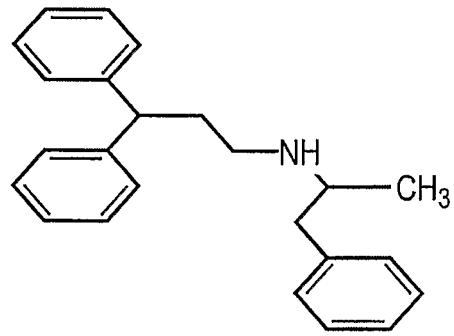
Figure 9:
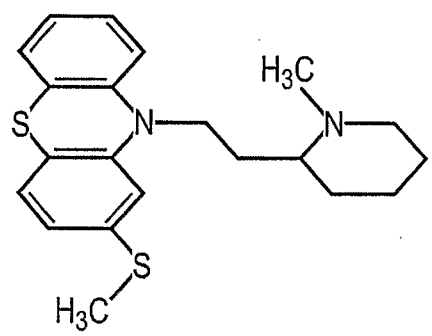
Figure 9:
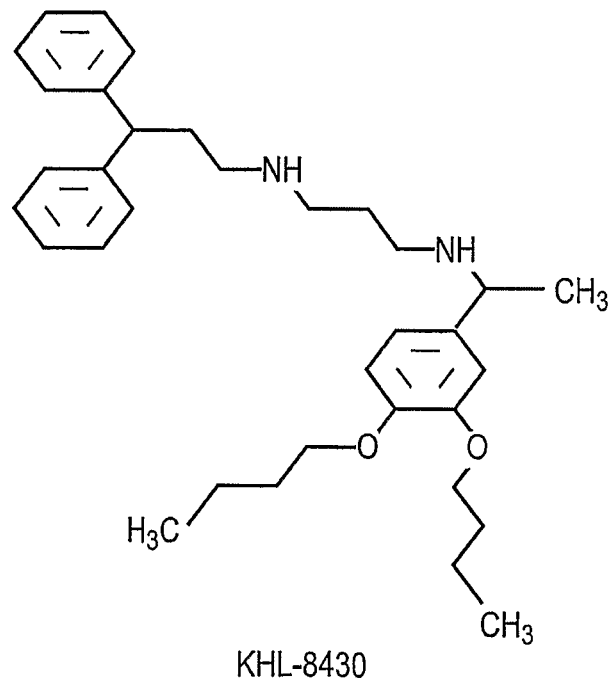

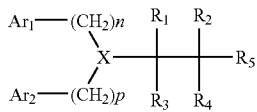

wherein $R_1$, $R_2$, $R_3$ and $R_4$ are independently H or lower alkyl; $R_5$ is aryl, heteroaryl, cycloalkyl, heterocycloalkyl, aryloxy, heteroaryloxy, cycloalkyloxy, heterocycloalkyloxy, arylamino, heteroarylamino, cycloalkylamino, heterocycloalkyl amino, arylthio, heteroarylthio, cycloalkylthio, heterocycloalkylthio, or cyclic olefin, any of which may be substituted or non-substituted; or substituted alkyl, substituted alkyl oxy or substituted alkyl amino wherein the substituent is an aryl, a heteroaryl, a cycloalkyl, heterocycloalkyl or a cyclic olefin, any of which may be substituted or non-substituted;
X is C or N;
n and p are independently whole numbers selected from 0, 1 and 2;
(CH$_2$)$_n$ and (CH$_2$)$_p$ may be substituted or non-substituted; and Ar$_1$ and Ar$_2$ are independently aryl or heteroaryl groups which may be substituted or non-substituted;
or a pharmaceutically acceptable salt or ester thereof;
with the proviso that when Ar$_1$ and Ar$_2$ are non-substituted phenyl, n and p are 0 and X is C, $R_5$ is not benzylmethylamino or 1-phenylprop-2-ylamino, when Ar$_1$ and Ar$_2$ are non-substituted phenyl, n and p are 0 and X is N, $R_5$ is not piperidine, and the compound is not KHL-8430 as shown in FIG. 9.

Unless specified otherwise, the term 'lower alkyl' shall be taken to mean an alkyl containing 4 or fewer carbon atoms, that is to say, methyl, ethyl, propyl or butyl. It preferably means methyl, ethyl or propyl, more preferably methyl or ethyl, most preferably methyl.

At least one of $R_1$, $R_2$, $R_3$ and $R_4$ may be lower alkyl, especially ethyl or methyl, most particularly methyl. In particular compounds, 1 of $R_1$, $R_2$, $R_3$ and $R_4$ is methyl, usually $R_1$ or $R_4$.

Alternatively, all of $R_1$, $R_2$, $R_3$ and $R_4$ may be H, and it is preferred that at least 1, more preferably at least 2, most preferably at least 3 are H.

Unless specified otherwise, the terms 'aryl', and 'cycloalkyl', whether in isolation or as part of another term such as 'aryloxy', 'arylamino', 'aralkyl', 'aralkylamino' and, shall be taken to mean a 4 to 10-membered, preferably 5 to 9-membered, more preferably 5 or 6-membered, most preferably a 6-membered, aromatic or cycloaliphatic ring system, containing one or more, preferably one, individual ring.

The terms 'heteroaryl' and 'heterocycloalkyl', whether in isolation or as part of another term, shall be taken, unless specified otherwise, to mean a 5 to 10-membered, preferably 5 to 9-membered, more preferably 5 or 6-membered, most preferably a 6-membered, aromatic or cycloaliphatic ring system, respectively, containing one or more, preferably one, individual ring and one or more, preferably one to three, more preferably one or two, most preferably one, heteroatom. It is particularly preferred that the one or more heteroatoms are N, S or O, especially N. When the heteroatom is N, it is preferred that the N is in the 1 or 2 positions, preferably the 2 position.

The term "cyclic olefin" shall be taken to mean, unless specified otherwise, a 5 to 10-membered, preferably a 6 to 10-membered ring system that contains at least one double bond. The system may be mono or bicyclic and may or may not be aromatic. The system may contain one or more heteroatoms, such as N, S and O, especially N. When the system contains N, it may be in the form of quaternary N, forming a quaternary ammonium or iminium group. In that instance, $R_5$ may, for example, be indolium or quinolium. Preferred cyclic olefins include indolium, methyl indolium, quinolium, methyl quinolium, isoquinolium and methyl isoquinolium.

Preferred aryls and heteroaryls include substituted or non-substituted phenyl, pyridinyl, indolium, isoindolium, quinolium and isoquinolium.

Preferred aryloxys and heteroaryloxys include phenyloxy and benzyloxy. Preferred arylthio and heteroarylthios include phenylthio and benzylthio.

Preferred arylaminos and heteroarylaminos include phenylamino and benzylamino.

As indicated above, $R_5$ may also be a substituted alkyl group, such as an aralkyl or a heteroaralky. The terms 'aralkyl' and 'heteroaralkyl' shall, unless otherwise specified, be taken to mean a lower alkyl substituted with an aryl or heteroaryl. Preferred aralkyls and heteroaralkyls include benzyl, pyridinylmethyl, phenylethyl and pyridinylethyl.

Preferred cycloalkyls and heterocycloalkyls include piperidinyl, piperazinyl piperidinylmethyl, piperidinylethyl, cycloalkylpyridinyl, pyrrolidinylethyl and methylpyrrolidinyl.

Figure 8:
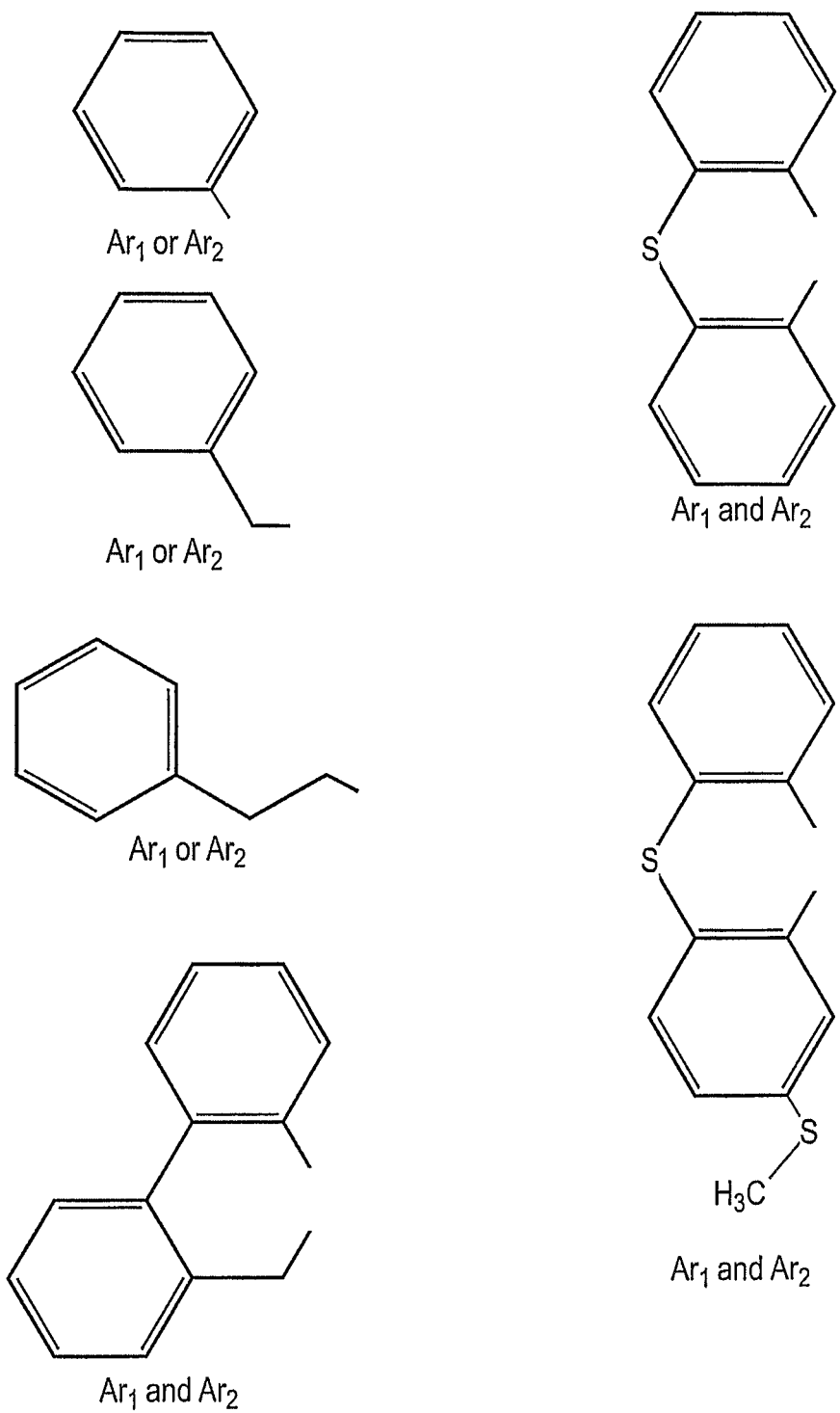

As indicated above, in particular, $R_5$ is selected from N-methylpiperidinylmethylamino, piperidinyl, phenyloxy, benzylmethyl, benzylmethylamino, phenylmethylamino, phenyl and N-methylpyrrolidinylethylamino. Preferred structures of $R_5$ are shown in FIG. 8.

Where $R_5$ is substituted, the substituent may be, for example, alkyl, particularly lower alkyl.

When one or both of Ar$_1$ and Ar$_2$ are substituted, the substituent may be independently, halogen, alkyl, alkenyl, alkynyl, alkoxy, haloalkoxy, hydroxyl, alkylthio, particularly methylthio or ethylthio. When the substituent is methylthio, it is preferably at position 2 or position 3.

Ar$_1$ and Ar$_2$ are preferably, independently, selected from phenyl, and methylthiophenyl. Ar$_1$ and Ar$_2$ may be joined to each other via atoms such as sulphur, or via carbon chains. For example, Ar$_1$ and A$_2$ may be joined so as to create a polycyclic structure, such as dihydrophenanthrene or dihydroanthracene. When one of Ar₁ and Ar₂ is phenyl and the other is methylthiophenyl, the aromatic rings are preferably connected via a sulphur atom, a sulphur bridge being formed between the 2 positions on each ring. In that case, the methylthio group is preferably at position 5. Preferred structures of Ar₁ and Ar₂ are shown in the compounds in FIG. 10.

n and p are preferably independently 0 or 1, more preferably 0.

Where compounds of the invention exist in different enantiomeric and/or isomeric forms, these compounds may be prepared as isomeric mixtures or racemates, although the invention relates to all optical isomers, whether present in an optically pure form or as mixtures with other optical isomers. Individual enantiomers may be obtained by methods known in the art, such as optical resolution of products or intermediates (for example chiral chromatographic separation (e.g. chiral HPLC)), or an enantiomeric synthesis approach. In general, where the positions of the heteroatoms in an heteroaryl or heterocycloalkyl group are not specified, it is to be understood that all chemically acceptable arrangements of those heteroatoms are intended to be covered.

Figure 10:
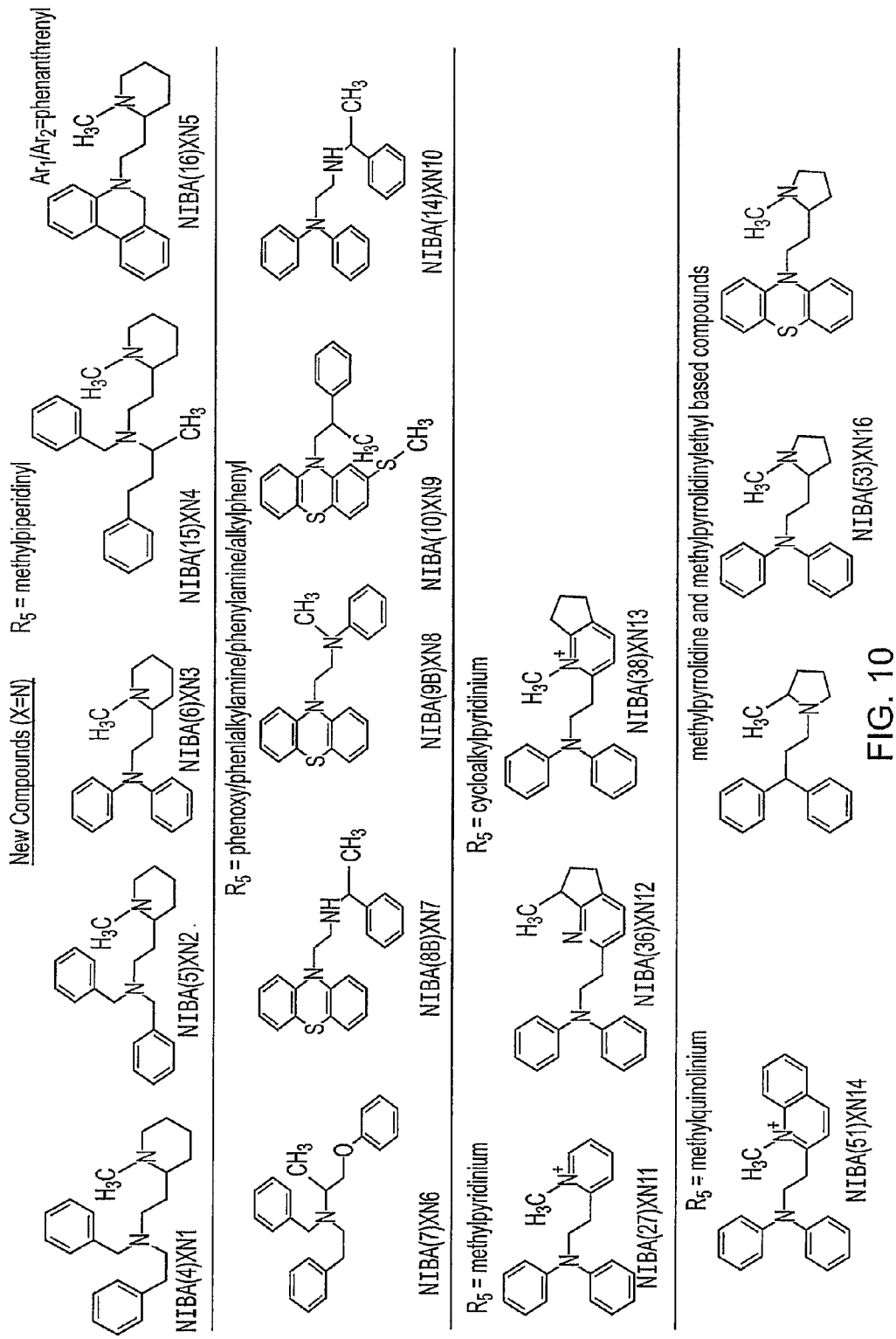
Figure 10:
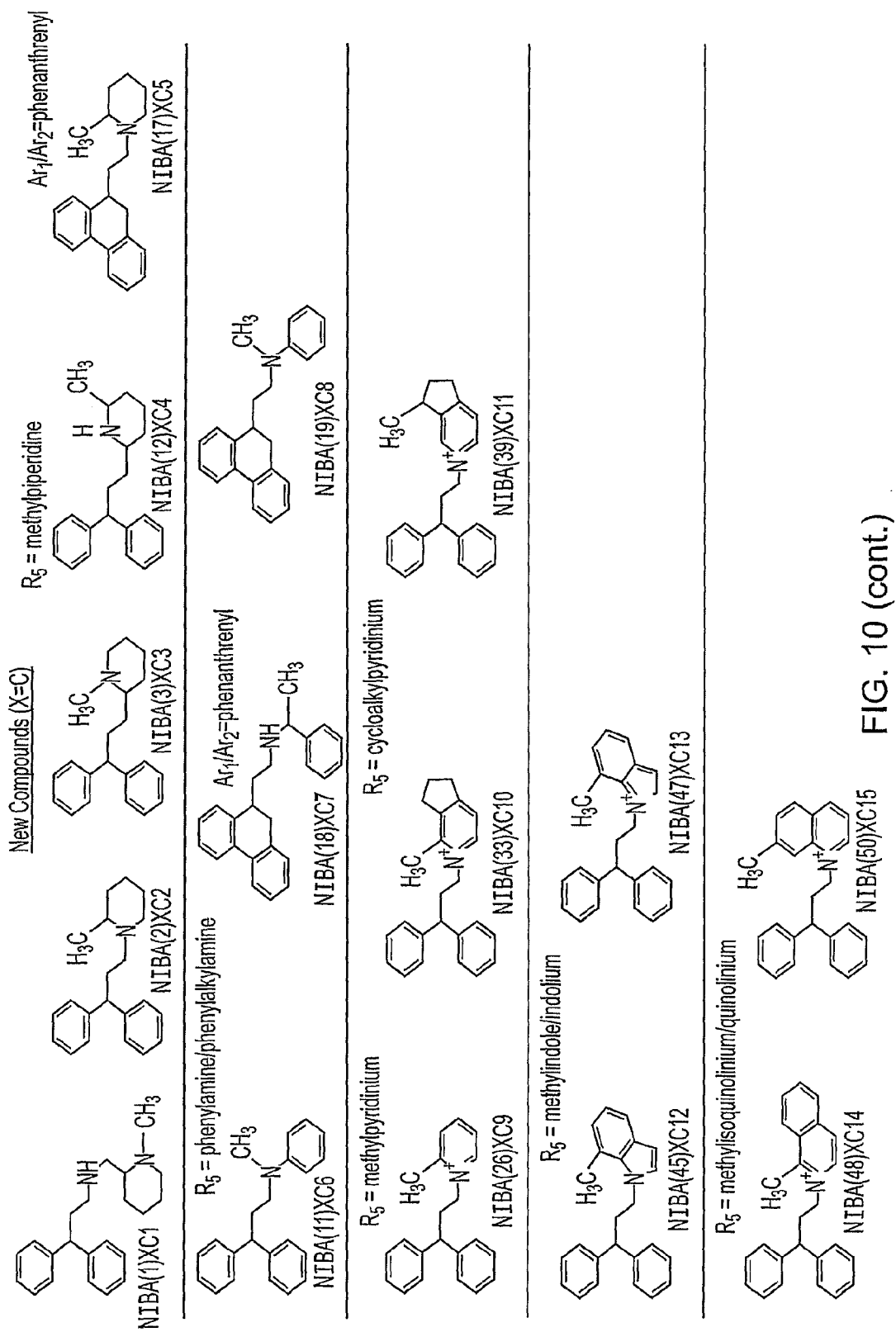

Preferred structures of formula I are shown in FIG. 10.

More preferred structures of formula I are NIBA(2)XC2, NIBA(1) XC1, NIBA(53)XN16, NIBA(6)XN3 and NIBA(14)XN10 as shown in FIG. 10.

In one embodiment, the invention is preferably not NIBA(2)XC2.

In another embodiment, the invention is preferably not NIBA(1)XC1.

In yet another embodiment, the invention is preferably not NIBA(53)XN16.

In a further embodiment, the invention is preferably not NIBA(6)XN3.

In another embodiment, the invention is preferably not NIBA(14)XN10.

In yet another embodiment of the invention, the structures of formula I are preferably NIBA(1)XC1, NIBA(53)XN16, and NIBA(14)XN10.

The compound according to the invention is preferably not fendiline, prenylamine, thioridazine or KHL-8430. The structures of these compounds are shown in FIG. 9. Further, the compound is preferably not phenoxybenzamine.

Also provided is a pharmaceutical composition comprising a compound according to the invention, or a pharmaceutically acceptable salt or ester thereof, and a pharmaceutically acceptable vehicle or carrier.

Pharmaceutical compositions of this invention comprise any of the compounds of the present invention, and pharmaceutically acceptable salts and esters thereof, with any pharmaceutically acceptable carrier, adjuvant or vehicle. Pharmaceutically acceptable carriers, adjuvants and vehicles that may be used in the pharmaceutical compositions of this invention include, but are not limited to, ion exchangers, alumina, aluminium stearate, lecithin, serum proteins, such as human serum albumin, buffer substances such as phosphates, glycerine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The pharmaceutical compositions of this invention may be administered orally, parenterally, by inhalation spray, rectally, nasally, buccally, vaginally or via an implanted reservoir. Oral administration is preferred. The pharmaceutical compositions of this invention may contain any conventional non-toxic pharmaceutically-acceptable carriers, adjuvants or vehicles. The term parenteral as used herein includes subcutaneous, intracutaneous, intravenous, intramuscular, intra-articular, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant such as Ph. Helv or a similar alcohol.

The pharmaceutical compositions of this invention may be orally administered in any orally acceptable dosage form including, but not limited to, capsules, tablets, and aqueous suspensions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavouring and/or colouring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilising or dispersing agents known in the art.

Also provided are compounds according to the invention for use in therapy.

Also provided is the use of a compound having formula I

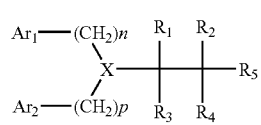

I wherein $R_1$, $R_2$, $R_3$ and $R_4$ are independently H or lower alkyl;

$R_5$ is aryl, heteroaryl, cycloalkyl, heterocycloalkyl, aryloxy, heteroaryloxy, cycloalkyloxy, heterocycloalkyloxy, arylamino, heteroarylamino, cycloalkylamino, heterocycloalkyl amino, arylthio, heteroarylthio, cycloalkylthio, heterocycloalkylthio, or cyclic olefin, any of which may be substituted or non-substituted; or substituted alkyl, substituted alkyl oxy or substituted alkyl amino wherein the substituent is an aryl, a heteroaryl, a cycloalkyl, a heterocycloalkyl or a cyclic olefin, any of which may be substituted or non-substituted;

X is C or N;

n and p are independently whole numbers selected from 0, 1 and 2; $(CH_2)_n$ and $(CH_2)_p$ may be substituted; and $Ar_1$ and $Ar_2$ are independently aryl or heteroaryl groups which may be substituted or non-substituted;

or a pharmaceutically acceptable salt or ester thereof;

with the proviso that when $Ar_1$ and $Ar_2$ are non-substituted phenyl, n and p are 0 and X is N, $R_5$ is not piperidine, in the preparation of a medicament for the reduction or prevention of the emission of sperm, or for the reduction or prevention of transmission of viral agents transmitted in seminal fluid.

The terms of formula I are as defined above.

The terms 'reduction or prevention of emission of sperm' shall be taken to mean that there is a reduction in the amount of sperm emitted during orgasm. In particular, there is a reduction in the volume of fluid ejaculated compared with normal ejaculation.

Accordingly, the medicament is useful for male contraception.

As emission of seminal fluid is reduced or inhibited, the medicament may also be used to reduce the transfer of viruses or other microbes found in seminal fluid material.

The medicament is preferably effective within at most 24 hours of being administered, more preferably at least 12 hours, more preferably at least 8 hours, most preferably at least 4 hours.

Also provided is a method of reducing or inhibiting sperm emission or ejaculation, or reducing or inhibiting transfer of viruses or microbes found in ejaculatory material comprising administering an effective amount of a compound having formula I

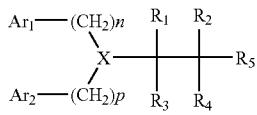

I wherein $R_1$, $R_2$, $R_3$ and $R_4$ are independently H or lower alkyl;

$R_5$ is aryl, heteroaryl, cycloalkyl, heterocycloalkyl, aryloxy, heteroaryloxy, cycloalkyloxy, heterocycloalkyloxy, arylamino, heteroarylamino, cycloalkylamino, heterocycloalkyl amino, arylthio, heteroarylthio, cycloalkylthio, heterocycloalkylthio, or cyclic olefin, any of which may be substituted or non-substituted; or substituted alkyl, substituted alkyl oxy or substituted alkyl amino wherein the substituent is an aryl, a heteroaryl, a cycloalkyl, a heterocycloalkyl or a cyclic olefin, any of which may be substituted or non-substituted;

X is C or N;

n and p are independently whole numbers selected from 0, 1 and 2; $(CH_2)_n$ and $(CH_2)_p$ may be substituted;

$Ar_1$ and $Ar_2$ are independently aryl or heteroaryl groups which may be substituted or non-substituted;

or a pharmaceutically acceptable salt or ester thereof;

with the proviso that when $Ar_1$ and $Ar_2$ are non-substituted phenyl, n and p are 0 and X is N, $R_5$ is not piperidine, or a pharmaceutically acceptable composition comprising such a compound to a subject.

The subject is preferably male. The subject is preferably human.

Figure 5A:
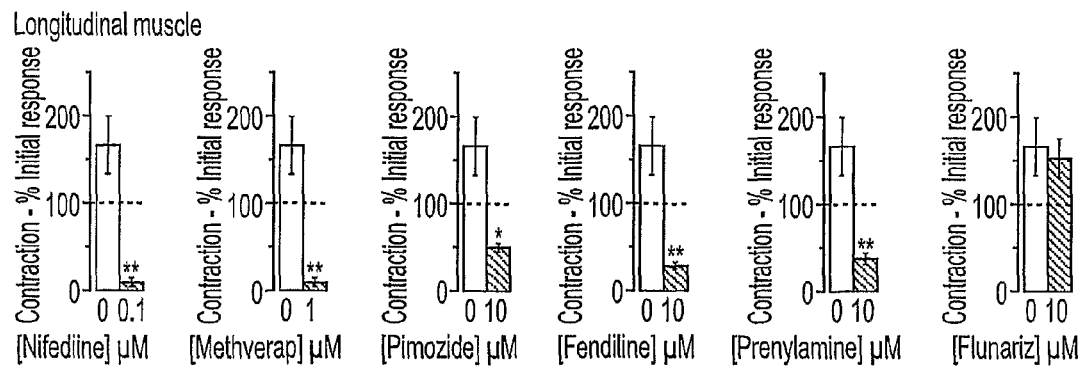
Figure 5B:
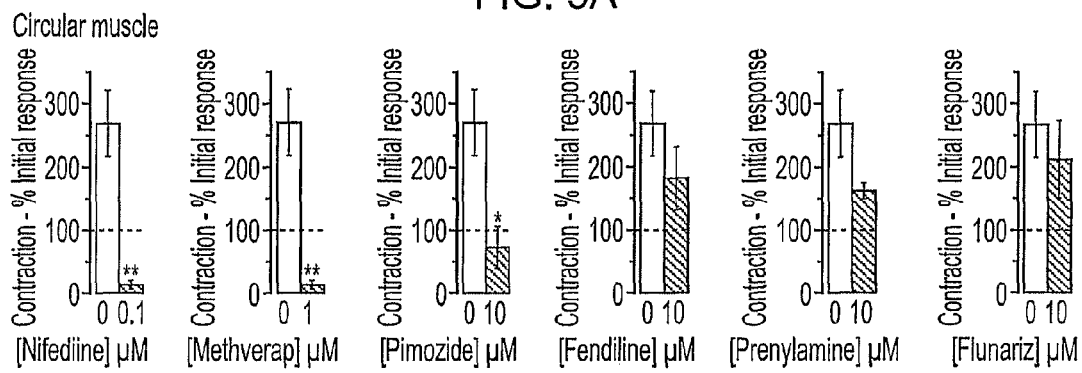
Figure 7:
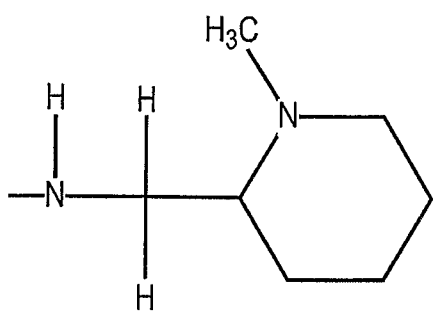
Figure 7:
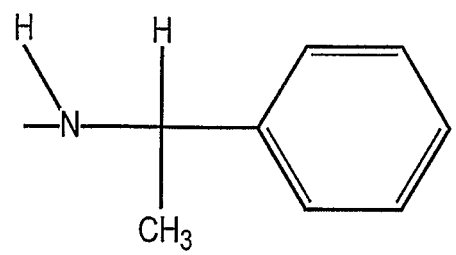
Figure 7:
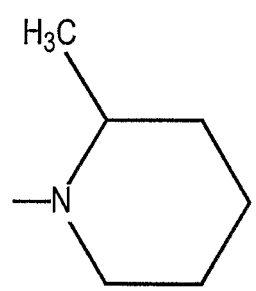
Figure 7:
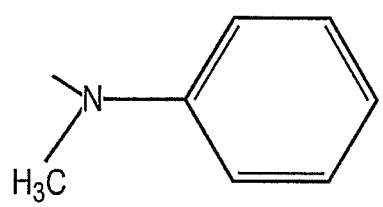
Figure 7:
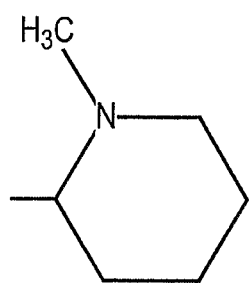
Figure 7:
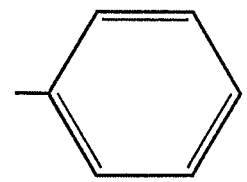
Figure 7:
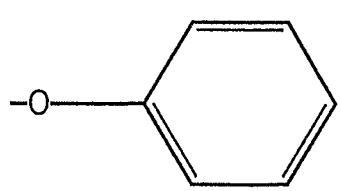
Figure 7:
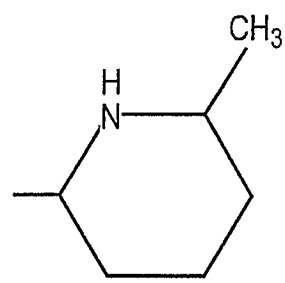
Figure 7:
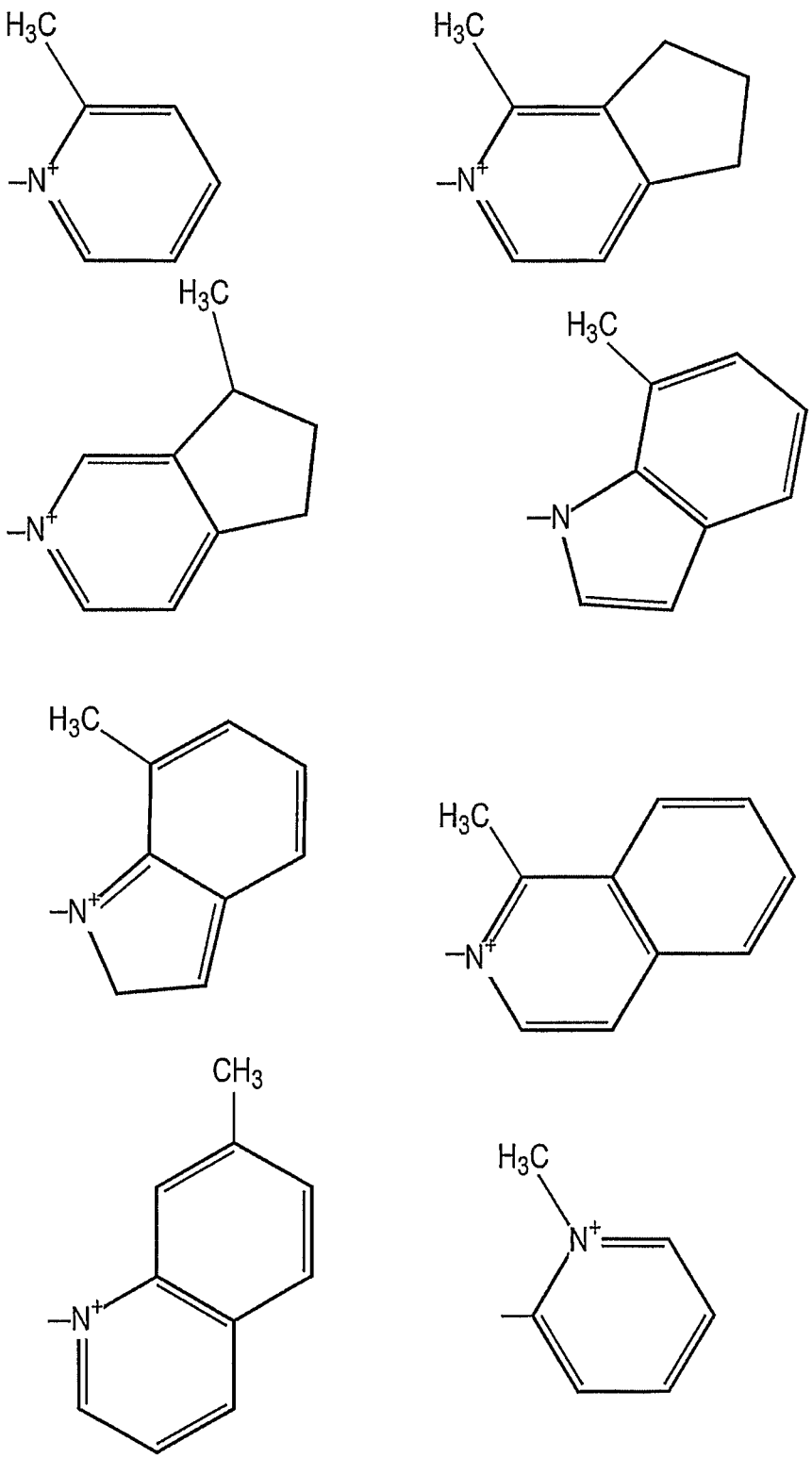
Figure 7:
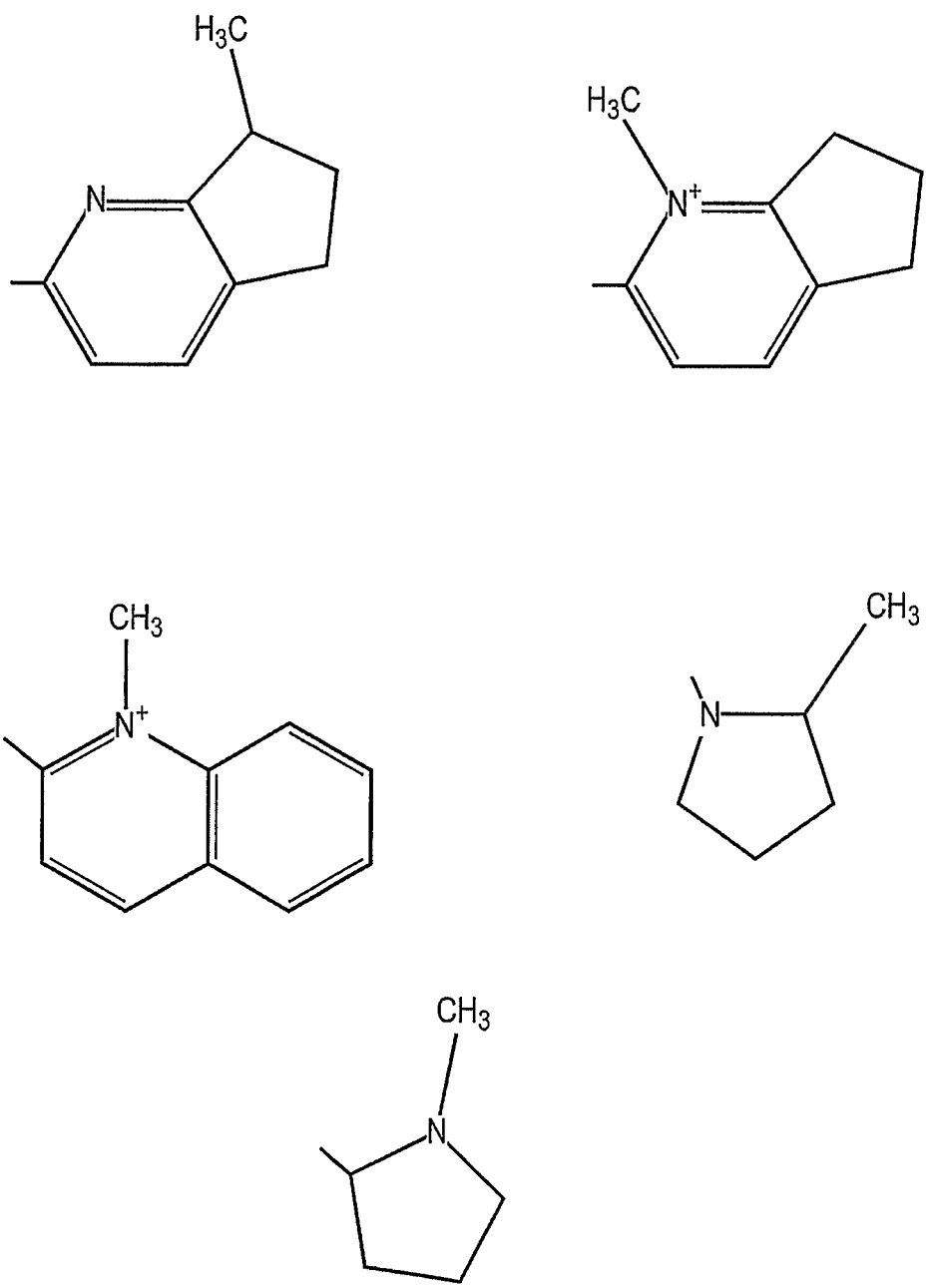

The invention will now be described in detail by way of example only, with reference to the figures, in which:

FIG. 1 shows (A) Sample record of contractility in longitudinal muscle of human vas deferens evoked by cumulative application of the L-type $Ca^{2+}$ agonist, FPL 64176 (0.1-10 µM). Following prolonged (~45 min) washout of FPL 64176 (indicated by double-line breaks), exposure to Krebs' medium containing increased concentration of potassium ($[K^+]_O$; 30 mM) promptly caused a tonic contraction associated with transient rhythmic contractility on the rising phase of the response. (B) Sample records from a different experiment showing potassium ($[K^+]_O$; 10, 30 & 120 mM)-induced contractions of longitudinal muscle (B-upper trace) in the absence and (B-lower trace) in the presence of FPL 64176 (1 µM, initial contact time 25 min). Horizontal bars below the response traces indicate period of exposure to elevated $[K^+]_O$;

FIG. 2 shows (A) Sample record of contractility in circular muscle of human vas deferens evoked by cumulative application of the L-type $Ca^{2+}$ agonist, FPL 64176 (0.1-10 µM). Following prolonged (~45 min) washout of FPL 64176 (indicated by double-line breaks), exposure to Krebs' medium containing increased concentration of potassium ($[K^+]_O$; 30 mM) promptly evoked a contractile response dominated by rhythmic contractility superimposed on an increased basal tone. (B) Sample records from a different experiment showing potassium ($[K^+]_O$; 10, 30 & 120 mM)-induced contractions of circular muscle (B-upper trace) in the absence and (B-lower trace) in the presence of FPL 64176 (1 µM, initial contact time 25 min). Horizontal bars below the response traces indicate period of exposure to elevated $[K^+]_O$;

FIG. 3 shows sample records of contractions evoked in longitudinal muscle of human vas deferens by high $[K^+]_O$ (30 & 120 mM) in the presence of FPL 64176 (1 µM). (A & C) show respectively the effects of the diphenylalkylamine, fendiline (10 µM) and the dihydropyridine nifedipine (0.1 µM). In panels A & C, the first record (upper traces) show contractions to $[K^+]_O$ (120 mM in drug-free Krebs' medium) before exposure to FPL 64176 (1 µM, contact time 25-30 min). In the continued presence of FPL 64176 (1 µM), the tissues were stimulated with $[K^+]_O$ (30 & 120 mM, Initial responses) and subsequently exposed to fendiline (10 µM) or nifedipine (0.1 µM, contact times of 25-40 min) or to drug-vehicle containing medium. In the continued presence of the drugs or drug-vehicle medium, the tissues were stimulated first with $[K^+]_O$ (120 mM, to explore use-dependent drug action) and 30-40 min later with $[K^+]_O$ (30 & 120 mM). Summary graphs (B & D) of the effects of repeated stimulation with high $[K^+]_O$ (120 mM) in the in the presence of FPL 64176 (1 µM) at the times indicated. Open bars are time-matched controls in drug vehicles (n=6) and hatched bars represent the additional presence of (B) fendiline (10 µM, n=8) or (D) nifedipine (0.1 µM, n=6). Contractions are expressed as a percentage of the initial response to high $[K^+]_O$ (120 mM) in the presence of FPL 64176 (1 µM) before exposure to drug-vehicle or the drugs (fendiline and nifedipine). Bars and lines represent mean±S.E.M;

FIG. 4 shows sample records of contractions evoked in circular muscle of human vas deferens by high $[K^+]_O$ (30 & 120 mM) in the presence of FPL 64176 (1 µM). (A & C) show respectively the effects of the diphenylalkylamine, fendiline (10 µM) and the dihydropyridine nifedipine (0.1 µM). In panels A & C, the first record (upper traces) show contractions to [K$^+$]$_O$ (120 mM in drug-free Krebs' medium) before exposure to FPL 64176 (1 μM, contact time 25-30 min). In the continued presence of FPL 64176 (1 μM), the tissues were stimulated with [K$^+$]$_O$ (30 & 120 mM, Initial responses) and subsequently exposed to fendiline (10 μM) or nifedipine (0.1 μM, contact times of 25-40 min) or to drug-vehicle medium. In the continued presence of the drugs or drug-vehicle medium, the tissues were stimulated first with [K$^+$]$_O$ (120 mM, to explore use-dependent drug action) and 30-40 min later with [K$^+$]o (30 & 120 mM). Summary graphs (B & D) show the effects of repeated stimulation with high [K$^+$]$_O$ (120 mM) in the in the presence of FPL 64176 (1 μM) at the times indicated. Open bars are time-matched controls in drug vehicles (n=6) and hatched bars indicate the additional presence of (B) fendiline (10 μM, n=6) or (D) nifedipine (0.1 μM, n=6). Contractions are expressed as a percentage of the initial response to high [K$^+$]$_O$ (120 mM) in the presence of FPL 64176 (1 μM) before exposure to drug-vehicle or the drugs (fendiline and nifedipine). Bars and lines represent mean±S.E.M;

FIG. 5 shows the effects of conventional L-type Ca$^{2+}$ antagonists and diphenylalkylamines on (A) longitudinal and (B) circular muscle contractions of human vas deferens to [K$^+$]$_O$ (30 mM) in the presence of FPL 64176 (1 μM). During superfusion with the drugs or drug-free/vehicle medium, the tissues were first stimulated with [K$^+$]$_O$ (120 mM) and subsequently by [K$^+$]$_O$ (30 mM). The contractions to [K$^+$]$_O$ (30 mM) are expressed as a percentage of the initial response evoked in the same preparation by [K$^+$]$_O$ (30 mM, in the presence of FPL 64176 but before exposure to the drug-containing medium). Bars and lines represent mean±S.E.M. Open bars indicate time-matched controls in longitudinal and circular muscle (n=6) and hatched bars are drug effects after exposure time of ~90 min. (Nifedipine 0.1 μM, longitudinal & circular muscle, n=6; Methoxyverapamil 1 μM, longitudinal & circular muscle, n=4; Pimozide 10 μM, longitudinal & circular muscle n=4; Fendiline 10 μM, longitudinal muscle, n=8 and circular muscle n=6; Prenylamine 10 μM, longitudinal muscle n=8, circular muscle n=5; Flunarizine 10 μM, longitudinal muscle n=6, circular muscle n=3);

FIG. 6 shows sample records of contractions evoked in (A) longitudinal and (B) circular muscle of human vas deferens by high [K$^+$]$_O$ (10, 30 & 120 mM) in the presence of Bay K 8644 (1 μM) and effects of the diphenylalkylamine, fendiline (10 μM). In panels A & B, the first record (upper traces) show contractions to [K$^+$]$_O$ (120 mM in drug-free Krebs' medium) before exposure to Bay K 8644 (1 μM, initial contact time ~25 min). In the continued presence of Bay K 8644 (1 μM), the tissues were stimulated with [K$^+$]$_O$ (10, 30 & 120 mM) and subsequently exposed to fendiline (10 μM). After a contact time of 30 min with the fendiline and in the continued presence of the drug, the tissues were stimulated first with [K$^+$]$_O$ (30 mM, to explore use-dependent drug action) and then with [K$^+$]$_O$ (10, 30 & 120 mM). The recurrent rhythmic activity induced in both longitudinal and circular muscle by Bay K 8644 (1 μM) were reliably blocked by fendiline (10 μM) only after prior use-dependent activation of the tissues with [K$^+$]$_O$ (30 mM);

FIG. 7 shows optional structures of R$_5$;
FIG. 8 shows optional structures of Ar$_1$ and Ar$_2$;
FIG. 9 shows prior art compounds; and
FIG. 10 shows optional structures of the compound of the invention.

EXAMPLE 1

Synthesis of the Compounds according to the Invention

The compounds of the invention could be synthesised by those skilled in the art using standard techniques and also using the teachings of Harsanyl, K., Korbonits, D., Kiss, P., 1964. Diphenylpropylamine derivatives. I. N-substituted 3,3-diphenylpropylamines. J. Med. Chem. 7, 623-625, which describes the synthesis of fendiline and Ehrhart, G., 1962. On the synthesis of diphenylalkylamines with coronary dilating action. Arch. Pharm. 295/67:196-205, which describes the synthesis of prenylamine.

Further, five of the compounds shown in FIG. 10, namely NIBA(2)XC2, NIBA(1)XC1, NIBA(53)XN16, NIBA(6)XN3 and NIBA(14)XN10, can be synthesised as follows:

Preparation and Synthetic Method for NIBA(1)XC1
[120153-c]

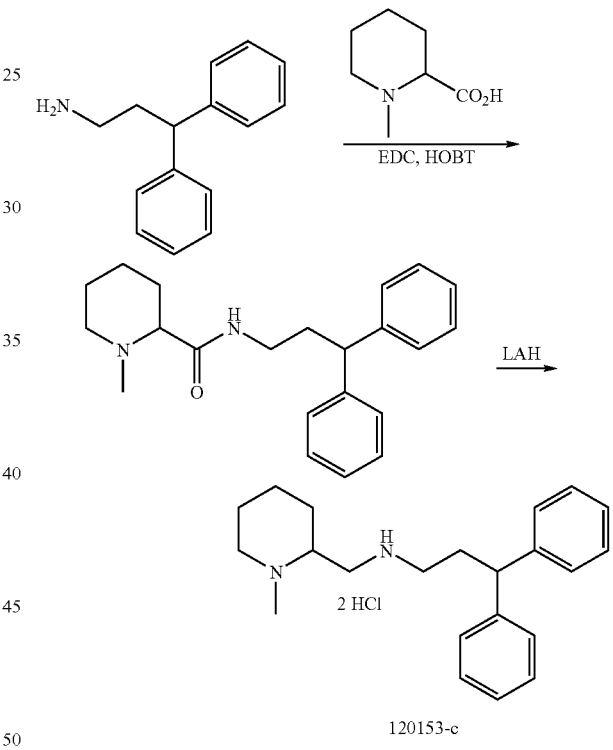

120153-c

Step 1
In a 3 necked flask under an atmosphere. of nitrogen, N-methylpiperidine-2-carboxylic acid hydrochloride (1.79 g, 10.0 mmol), HOBt (1.35 g, 10 mmol). EDC hydrochloride (1.92 g, 10 mmol) and TEA (3.00 g, 30 mmol) were dissolved in CH$_2$Cl$_2$ (100 mL, dry) at 0° C. After 30 min, diphenylpropylamine (2.11 g, 10 mmol) was added. After 1 more hour stirring at 0° C., the mixture was allowed to stir at rt overnight. When TLC showed consumption of (nearly) all starting materials, the reaction mixture was quenched with water (150 mL). The layers were separated and the organic layer was washed with NaHCO$_3$ (50 mL, sat.), dried (MgSO$_4$), filtered and concentrated in vacuo to yield a yellow/orange oil (4.12 g). This crude oil was purified by chromatography (Silica, CH$_2$Cl$_2$/CH$_3$OH, gradient 0-3%) to yield a colorless oil (2.6 g, 7.7 mmol).

Step 2

LiAlH$_4$ (0.40 g, 10.5 mmol) was suspended in THF (75 mL, dry) in a 3 necked flask under a nitrogen atmosphere. The suspension was cooled with an ice-salt bath to −10° C. before a solution of the amide from step 1 (2.43 g, 7.2 mmol) in THF (10 mL, dry) was added dropwise over (10 min. After addition, the suspensian was gradually heated to reflux overnight. The excess of LiAlH$_4$ was carefully decomposed by the addition of water (1 eq), NaOH (1 eq, 4N), and water (4 eq.) again. The suspension thus obtained was diluted with EtOAc and filtered over Celite. Concentration in vacuo yielded a colorless oil (2.38 g) which was purified by chromatography (Silica, CH$_2$Cl$_2$/CH$_3$OH, gradient 1-5%). The pure free base (1.00 g) was converted to the dihydrochloride by treatment of the free base in CH$_2$Cl$_2$ (10 mL) with HCl (4 mL 5-6N in 2-propanol), yielding a white solid foam (1.10 g, 2.78 mmol). To obtain a nice solid and remove traces of solvent (visible in NMR initially), the foam was dissolved in a minimum amount of water, concentrated in vacuo and subsequently solidified with diethyl ether. This yielded a white solid (1.10 g, 2.78 mmol).

Preparation and Synthetic Method for
NIBA(14)XN10 [120153-f]

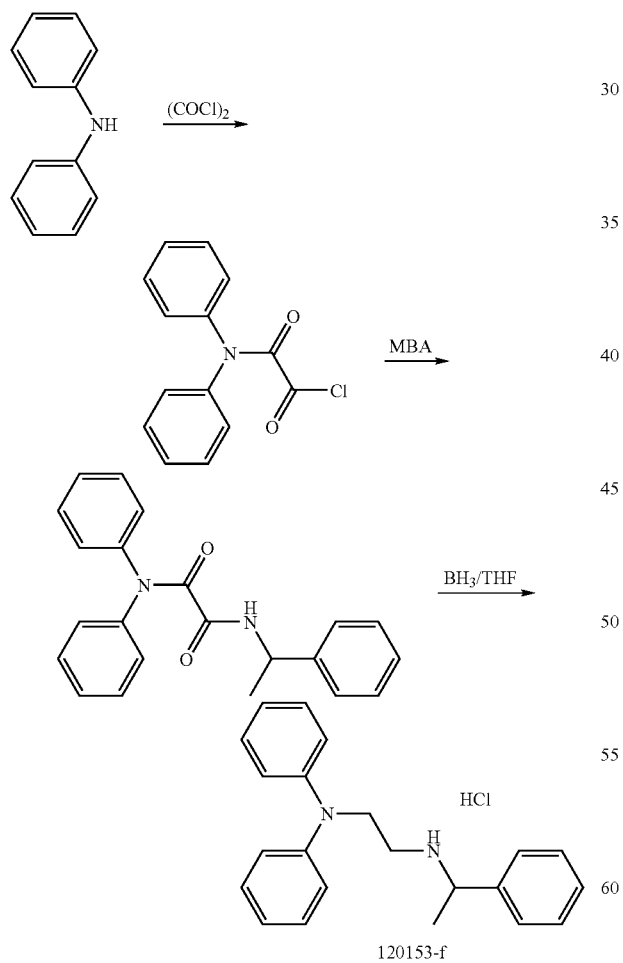

120153-f

Step 1 and 2

Oxalylchloride (4 mL) was dissolved in CH$_2$Cl$_2$ (20 mL) and cooled to 0° C. with an ice bath. Diphenylamine (5.00 g, 29.6 mmol) was added portionwise over 5 min. After 15 min at 0° C., the reaction was allowed to stir at rt for 2 hr. The volatiles were then removed in vacuo. The residual brown oil (7.64 g) was diluted in CH$_2$Cl$_2$ (50 mL) and cooled to 0° C. with an ice bath. TEA (5 mL) was added dropwise, followed by the dropwise addition of racemic alpha-methylbenzylamine (3.58 g, 29.6 mmol). The cooling was removed and the dark mixture was allowed to stir at rt for 30 min before quenching with water (100 mL). The organic layer was separated, and the water layer was extracted with CH$_2$Cl$_2$ (2*50 mL). The combined extracts were dried (MgSO$_4$), filtered and concentrated to yield a beige solid (11.00 g) that was crystallized from ethanol to yield the pure N,N-Diphenyl-N'-(1-phenyl-ethyl)-oxalamide (6.72 g, 19.6 mmol) as an off white solid.

Step 3

In a three necked flask with dropping funnel and condenser under a nitrogen atmosphere, N,N-Diphenyl-N'-(1-phenyl-ethyl)-oxalamide (6.00 g, 17.5 mmol) was dissolved in THF (75 mL, dry). The solution was cooled with an ice bath to 0° C. BH$_3$ (75 mL, 1N in THF) was added dropwise over 20 min. After the addition, the mixture was allowed to warm to rt and subsequently heated to a gentle reflux overnight. When no more SM was detectable by TLC, the mixture was cooled to rt and carefully quenched with water to decompose the excess of BH$_3$. The volatiles were removed in vacuo, and the residue was treated with HCl (100 mL, 4N) to decompose the product-borane complex. When gas formation ceased, the pH of the water layer was adjusted to pH 10 (NaOH, 4N), and extracted with CH$_2$Cl$_2$ (4*75 mL). The combined extracts were dried (MgSO$_4$), filtered and concentrated in vacuo. This yielded the crude product as an oil (5.80 g). Purification by chromatography (Silica, CH$_2$Cl$_2$/CH$_3$OH, gradient 0-3%) yielded the pure free base (2.60 g, 8.23 mmol). The mono hydrochloride salt was obtained by treatment of a solution of the free base in DCM with HCl (5-6 N in 2-propanol) as a white solid.

Preparation and Synthetic Method for NIBA(6)XN3
[120153-e]

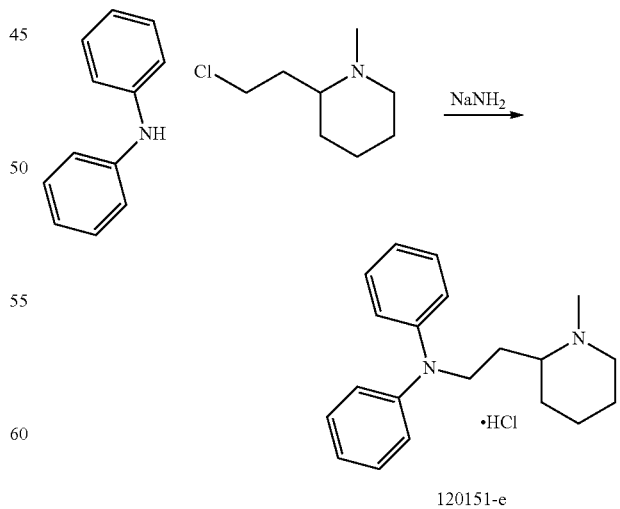

120151-e

2-Chloroethyl-2-(N-methylpiperidine) hydrochloride (2.5 g, 12.8 mmol), NaNH$_2$ (2.00 g, 51.0 mmol), and diphenylamine (2.16 g, 13.6 mmol) were suspended in toluene (75 mL, dry) under a nitrogen atmosphere and set to reflux over the weekend in a round bottom flask with condenser. When the conversion reached around 60%, the reaction mixture was cooled to rt, and solids were removed by filtration. The organic layer was extracted with HCl (3*30 mL, 2N). Subsequently, the combined water layers were treated with NaOH (4N) to adjust the pH to 10. Extraction with $CH_2Cl_2$ (3*75 mL, general drying procedure and concentration) yielded the crude 120153-e as an oil (3.10 g). which was purified by chromatography (Silica, $CH_2Cl_2/CH_3OH$, gradient 1-3%) to yield the pure free base. (2.10 g, 7.14 mmol). The mono hydrochloride salt was obtained by treatment of a solution of the free base in DCM with HCl (5-6N in 2-propanol) as a hygroscopic grey green solid.

Preparation and Synthetic Method for NIBA(2)XC2 [120153-a]

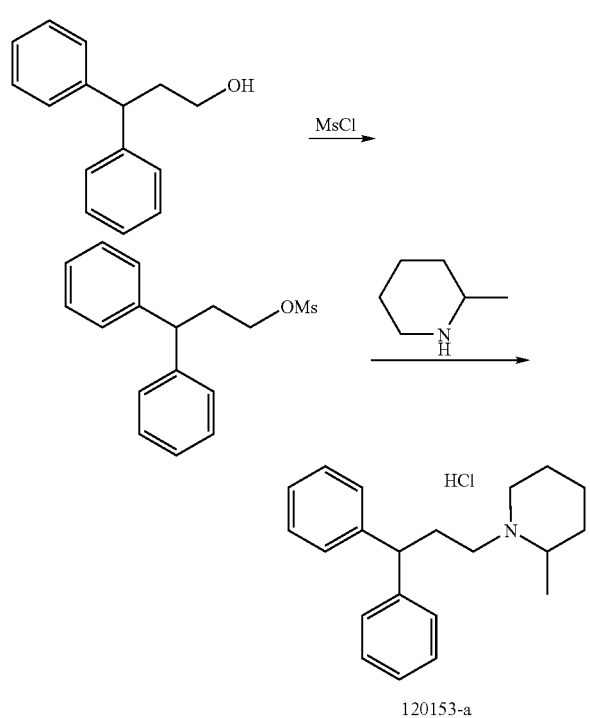

120153-a

Step 1

In a round bottom flask under a nitrogen atmosphere, 3,3-Diphenylpropan-1-ol (5.00 g, 23.6 mmol) and TEA (7.15 g, 70.8 mmol) were dissolved in $CHCl_3$ (75 mL, dry). The solution was cooled with an ice-salt bath to −15° C. Methane sulphonylchloride (6.72 g, 59.0 mmol) was added dropwise over a period of 10 min. The solution was gradually allowed to warm to 0° C. and stored in the fridge at 4° C. overnight. The yellow/orange solution was then quenched with ice-water (ca 150 mL) and the layers were separated. The water layer was washed with $CH_2Cl_2$ (2*75 mL), and the combined organic layers were dried ($MgSO_4$), filtered and concentrated in vacuo at 20° C. This yielded an oil that solidified upon standing (8.16 g). The solid was ground, triturated with petroleum ether (50 mL) and the solid was collected by filtration (7.90 g off-white solid).

Step 2

In a 3 necked flask under an atmosphere of nitrogen, 2-methylpiperidine (1.35 g, 13.6 mmol) was dissolved in acetonitrile (75 ml, dry) at 5° C. The mesylate obtained in the first step (3.95 g, 13.6 mmol) was added portionwise over 5 min. After 30 min, the cooling was removed and the solution was gradually heated to reflux for 24 h. The volatiles were removed by filtration and the residue was treated with HCl (2N, 75 ml). The water layer was washed (ether, 2*50 mL) and then treated with NaOH (4N) to adjust the pH to 10. Extraction with $CH_2Cl_2$ (3*75 mL), drying ($MgSO_4$), filtration and evaporation of the volatiles yielded the crude target 120153-a as an oil (2.42 g), which was purified by chromatography (Silica, $CH_2Cl_2/CH_3OH$, gradient 0-2%). The pure free base thus obtained (2.00 g, 6.8 mmol) was converted to the HCl salt and isolated as a light yellow solid (2.24 g, 6.79 mmol).

Preparation and Synthetic Method for NIBA(53)XN16 [120153-d]

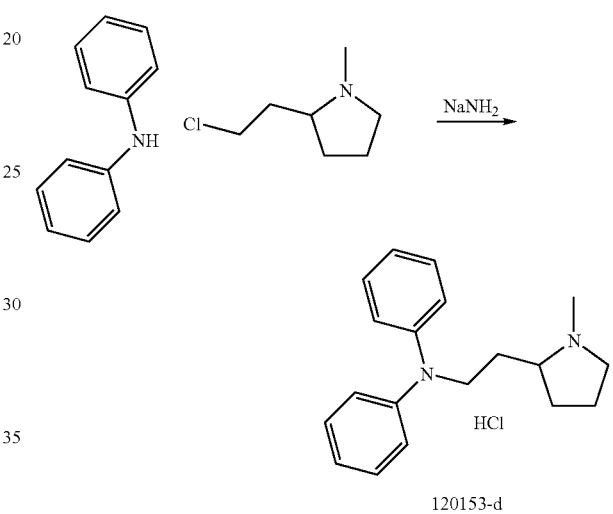

120153-d

2-Chloroethyl-2-(N-methylpyrrolidine) hydrochloride (2.5 g, 13.6 mmol), $NaNH_2$ (2.10 g, 53.8 mmol), and diphenylamine (2.30 g, 13.6 mmol) were suspended in toluene (75 mL, dry) under a nitrogen atmosphere and set to reflux over the weekend in a round bottomed flask with condenser. When the conversion reached around 50%, the reaction mixture was cooled to rt, and solids were removed by filtration. The organic layer was extracted with HCl (3*20 mL, 2N). Subsequently, the combined water layers were treated with NaOH (4N) to adjust the pH to 10. Extraction with $CH_2Cl_2$ (3*75 mL, general drying procedure and concentration) yielded the crude 120153-d as an oil (1.97 g), which was purified by chromatography (Silica, $CH_2Cl_2/CH_3OH$, gradient 1-3%) to yield the pure free base (0.95 g, 3.4 mmol). The mono hydrochloride salt was obtained by treatment of a solution of the free base in DCM with HCl (5-6N in 2-propanol) as a light pink solid.

EXAMPLE 2

Contractile Actions of L-type $Ca^{2+}$-Agonists in Human Vas Deferens and Effects of L-type $Ca^{2+}$-Antagonists, Diphenylalkylamines and Phenothiazines Materials and Methods Preparation of Tissues Human vas deferens specimens were obtained after elective vasectomies of healthy fertile men. College ethical approval and the consent of patients were obtained. The specimens were placed in ice-cold Krebs' medium, dissected-free of connective tissue/blood vessels and cut longitudinally into strips (longitudinal muscle preparations; 5-10 mm long & 1 mm wide) or transversely into rings (circular muscle preparations; 3 mm in length). The longitudinal and circular muscle preparations were then set up for tension recording (resting tension 5-7 mN) in a Perspex chamber superfused at 2 ml per min with Krebs' medium (36° C.) composed of (mM): NaCl, 118.8; $NaHCO_3$, 25; KCl, 4.7; $CaCl_2.2H_2O$, 2.5; $KH_2PO_4$, 1.2; $MgSO_4.7H_2O$, 1.2; glucose, 11.1; ascorbic acid 0.1 and continuously gassed with 95% $O_2$ and 5% $CO_2$. Contractile responses were recorded via a Harvard-type force-displacement transducer. The analog signals were digitised using CIO-Das 16/Jr data acquisition software (Amplicon Liveline, Brighton, UK) and re-plotted on a microcomputer.

Experiments with L-Type $Ca^{2+}$ Agonists and High $[K^+]_o$

Tissues were equilibrated for 180 min in Krebs' medium containing inhibitors of extraneuronal and neuronal reuptake of noradrenaline, oestradiol (1 µM) and desipramine (0.1 µM) respectively, inhibitors of catechol-O-methyltransferase and monoamine oxidase, tropolone (10 µM) and iproniazid (10 µM) respectively and the β-adrenoceptor blocker, propranolol (1 µM). At the end of the equilibration period, the tissues were stimulated with noradrenaline (100 µM). Subsequently, the tissues were superfused and maintained throughout the experimental period in Krebs' medium containing the $\alpha_1$-adrenoceptor antagonist, prazosin (10 µM), the adrenergic neuron blocker, guanethidine (10 µM,) and tetrodotoxin (0.1 µM). After a contact time of 30-40 min in this medium, different experimental protocols (described below) were adopted in order to (a) Elucidate the contractile actions of L-type $Ca^{2+}$ agonists such as FPL 64176 or Bay K 8644. In these experiments, tissues were exposed to FPL 64176 (0.1-10 µM added cumulatively) or in separate experiments Bay K 8644 (0.1-10 µM added cumulatively).

(b) Investigate the effects of various diphenylalkylamines and conventional L-type $Ca^{2+}$ antagonists (methoxyverapamil or nifedipine) on contractions evoked by high concentrations of extracellular potassium (high $[K^+]_o$) in the presence of L-type $Ca^{2+}$ agonists, FPL 64176 (1 µM) or Bay K 8644 (1 µM). In this protocol, tissues were stimulated with high $[K^+]_O$ (10, 30 and 120 mM at 10-15 min intervals) in normal Krebs' medium, then exposed to L-type $Ca^{2+}$ agonists for 20-30 min and subsequently stimulated with high $[K^+]_O$ (10, 30 and 120 mM) in the presence of the drugs. These provided the initial responses. Following this and in the continuous presence of the L-type $Ca^{2+}$ agonists, the tissues were exposed additionally to L-type $Ca^{2+}$ antagonists (conventional or diphenylalkylamines) or drug-free vehicle medium. After contact times of 25-50 min the tissues were stimulated, first with high $[K^+]_O$ (either 30 mM or 120 mM) in order to take account of the well-documented use-dependent action of the diphenylalkylamine $Ca^{2+}$ antagonists [71, 77]. Following recovery from the test contraction and after a further 30-40 min, the tissues were then stimulated with high $[K^+]_o$ (10, 30 and 120 mM). This protocol is illustrated in FIGS. 3 and 4. The resulting contractions were measured (see below) and expressed as a percentage of corresponding initial responses to high $[K^+]$o evoked in the presence of L-type $Ca^{2+}$ agonists (i.e. before exposure to L-type $Ca^{2+}$ antagonists). Contractions obtained in experiments carried out in the presence of the L-type $Ca^{2+}$ agonists but without L-type $Ca^{2+}$ antagonists (drug-free/vehicle medium) were expressed in a similar manner to obtain time-matched controls. Subsequent analysis (see below) was between contractions of drug-treated tissues and time-matched controls (c) Determine the inhibitory potencies ($IC_{50}$ values) of various diphenylalkylamines and phenothiazines and conventional L-type $Ca^{2+}$ antagonists (nifedipine and methoxyverapamil) against contractions evoked in longitudinal and circular muscle of human vas deferens by high $[K^+]_o$ (120 mM) in the presence of FPL 64176. In these experiments, tissues were stimulated with high $[K^+]_o$ (120 mM); sequentially in normal Krebs' medium and after 25-30 min exposure to the L-type $Ca^{2+}$ agonist, FPL 64176, (1 µM, Initial response). In the continuous presence of the L-type $Ca^{2+}$ agonist, the tissues were exposed to cumulative concentrations of various drugs (diphenylalkylamines, phenothiazines or conventional L-type $Ca^{2+}$ antagonists, in separate experiments) or to Krebs' medium containing drug vehicles (time-matched controls). In order to take account of use-dependent drug action, the tissues were stimulated twice with high $[K^+]$o (120 mM) during exposure to each concentration of the drugs (initial contact time, 30-40 min and subsequently 35-40 min after the first response). The two contractions evoked by high $[K^+]_o$ (120 mM) at each concentration of the drugs or during corresponding time-matched controls were measured (see below) and expressed as a percentage of the initial response evoked by high $[K^+]_o$ (120 mM in the presence of FPL 64176, 1 µM). Corresponding time-matched controls were measured in a similar manner. Mean percentage inhibition of the two contractions at each concentration of the L-type $Ca^{2+}$ antagonists was calculated with respect to corresponding time-matched controls and concentrations producing 50% reduction of the contractions ($IC_{50}$ values) were determined by linear regression.

Measurements and Statistical Analysis

The contractions were measured using computer software developed in-house to measure the total response (i.e. rhythmic activity plus tonic contraction). The results are given as means±S.E.M. and n refers to the number of tissues used in each experiment Statistical differences between two groups were analysed using Student's t test. With more than two groups, statistical comparison was by a one-way analysis of variance (ANOVA) followed by a priori comparisons with Student's t-test using the within groups variance from ANOVA. Differences between the mean of drug-free control and experimental groups were considered significant at $P<0.05$.

Drugs

Drugs used were as follows: noradrenaline tartrate (Winthrop Laboratories, Guildford, Surrey, UK), propranolol hydrochloride (ICI, Macclesfield, Cheshire, UK), thioridazine hydrochloride and sulphoridazine (Novartis Pharma AG, Switzerland), (S)-(–)-Bay K 8644 ((4S)-1,4-dihydro-2,6-dimethyl-5-nitro-4-[2-trifluoromethyl)-phenyl]-3-pyridinecarboxylic acid methyl ester), pimozide and prazosin hydrochloride (Tocris, UK), chlorpromazine hydrochloride and trifluoperazine dihydrochloride (Research Biochemicals International, Natick, Mass., USA). FPL 64176 (2,5-dimethyl-4-[2-(phenylmethyl)benzoyl]-H-pyrrole-3-carboxylic acid methyl ester), desipramine hydrochloride, 17β-oestradiol, dimethyl sulfoxide (DMSO), guanethidine monosulphate, tetrodotoxin (TTX), tropolone, iproniazid hydrochloride, ascorbic acid, nifedipine, (–)-methoxyverapamil hydrochloride, fendiline hydrochloride, prenylamine lactate, flunarizine dihydrochloride and cinnarizine all from Sigma (Poole, UK). Stock solutions of desipramine, tropolone, iproniazid, TTX, guanethidine and (–)-methoxyverapamil were prepared in distilled water and other drugs in DMSO or ethanol. Aliquots added to drug perfusates or vehicle controls had a final DMSO or ethanol concentration of less than 0.01%. Solutions containing high concentrations of potassium were prepared by isosmotic replacement of NaCl with KCl.

Results

Contractile Actions of L-Type $Ca^{2+}$-Agonists

Figure 1B:
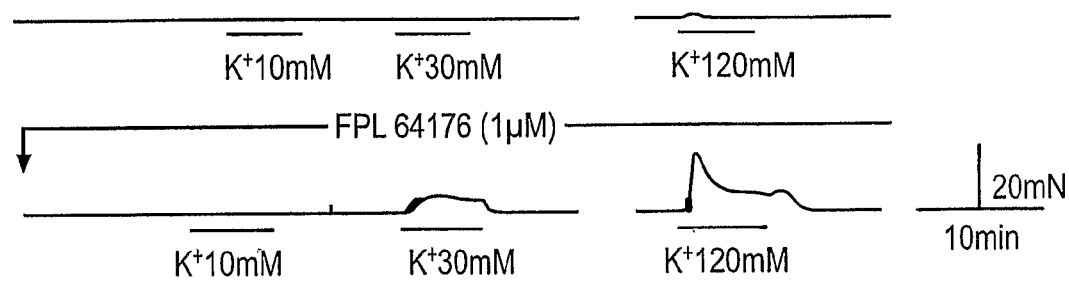
Figure 2A:
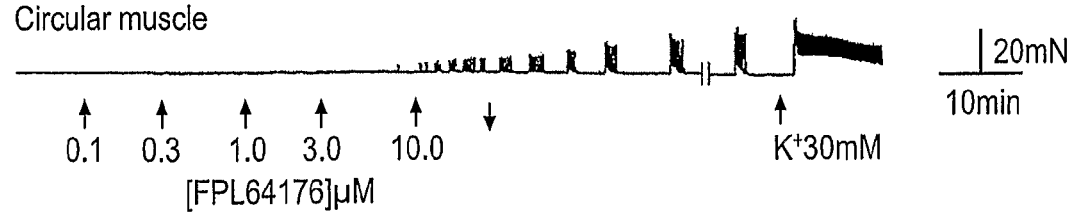

FIGS. 1 & 2 show the contractile actions of the L-type $Ca^{2+}$-agonist, FPL 64176 (0.1-10 μM) in longitudinal (FIG. 1A) and circular muscle (FIG. 2A) of human vas deferens. Both muscle types were quiescent to brief (~10 min) exposure to FPL 64176 (0.1-3 μM). Higher concentrations of FPL 64176 (10 μM) produced rhythmic contractility of both muscle types. Following 40-45 min washout of FPL 64176, stimulation of the tissues with high concentration of potassium ($[K^+]_O$, 30 mM) promptly evoked contractions which were remarkably different in longitudinal and circular muscles (FIGS. 1A & 2A). The prompt activation by $[K^+]_O$, (30 mM) presumably indicates that the effects of exposure to FPL 64176 is not readily reversible (see section, $[K^+]_O$, 30 mM in drug-free medium). Experiments with a different L-type Ca 2-agonist, Bay K 8644 (0.1-10 μM) produced effects that were qualitatively comparable to the actions of FPL 64176; both longitudinal and circular muscles were unresponsive to brief exposure to Bay K 8644 (0.1-3 μM) and rhythmic contractility was observed with higher concentrations of Bay K 8644 (10 μM, not shown). In subsequent experiments, FPL 64176 or Bay K 8644 at a concentration of 1.0 μM was used and prolonged exposure (≥20 min) produced recurrent rhythmic contractility in some tissues. These were readily inhibited by conventional L-type $Ca^{2+}$-antagonists (nifedipine, 0.1 μM or methoxyverapamil, 1 μM).

Effects of L-type $Ca^{2+}$-Agonists on Contractions to Increased Concentrations of Potassium ($[K^+]_O$)

Figure 2B:
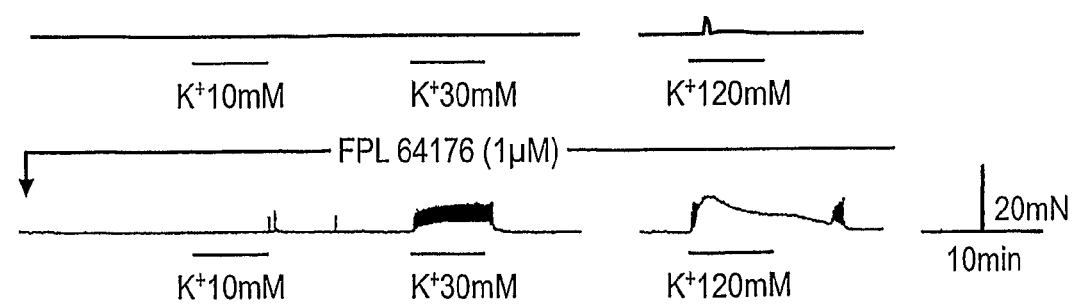

In normal Krebs' medium (absence of L-type $Ca^{2+}$-agonists), exposure to $[K^+]_O$, (10 mM or 30 mM) generally produced no detectable response in longitudinal muscle (FIG. 1B) or in circular muscle (FIG. 2B). However in some tissues, $[K^+]_O$ (30 mM) evoked transient rhythmic contractility of longitudinal or circular muscle (not shown). Higher $[K^+]_O$ (120 mM) produced tonic contractions of both muscle types that was associated with brief rhythmic contractility on the rising phase of the responses (FIGS. 1B & 2B). Following 25-30 min exposure of the tissues to FPL 64176 (1.0 μM) and in its continuous presence, $[K^+]_O$ (10 mM) caused either brief rhythmic contractility of both muscle types or no detectable response (FIGS. 1B & 2B). In the presence of the L-type $Ca^{2+}$-agonist, exposure to $[K^+]_O$ (30 mM) reliably evoked contractions of both longitudinal and circular muscles and $[K^+]_O$ (120 mM) evoked contractions that were markedly enhanced relative to the corresponding response in FPL-free Krebs' medium. The contractions were followed (after ~15-20 min) by recurrent rhythmic contractility in some experiments (not shown). Furthermore, as shown in FIGS. 1B & 2B, the contractions evoked by $[K^+]_O$ (30 mM) or $[K^+]_O$ (120 mM) had different profiles in longitudinal and circular muscle. In longitudinal muscle (FIG. 1B), the contractions to $[K^+]_O$ (30 mM) consisted of an increase in basal tension preceded in some tissues by brief bursts of rhythmic contractility. Higher $[K^+]_O$ (120 mM) produced tonic contractions that developed and declined rapidly to a sustained tonic response (FIG. 1B). The time to peak from onset of the response and time of decline from peak to half maximum tension respectively were 0.89±0.1 min and 1.53±0.2 min (n=10).

In circular muscle (FIG. 2B), the contraction evoked by $[K^+]_O$ (30 mM) in the presence of FPL 64176 (1.0 μM) consisted of continuous rhythmic activity superimposed on a tonic contraction. Higher $[K^+]_O$ (120 mM) produced tonic contractions, which developed and declined more slowly (P<0.05) than in longitudinal muscle (FIG. 2B compared with FIG. 1B). The time to peak from onset of the response and time of decline from peak to half maximum tension respectively were 2.02±0.2 min and 4.77±0.8 min (n=10). Following the first series of responses, a second exposure to $[K^+]_O$ (30 mM & 120 mM) in the continuous presence of FPL 64176 (1.0 μM) produced contractions that were enhanced relative to the initial or corresponding first response evoked in the presence of the L-type $Ca^{2+}$-agonist. For example in the continuous presence of FPL 64176 (1.0 μM), the second exposure to $[K^+]_O$ (30 mM & 120 mM) evoked contractions that measured 160-181% and 270-300% of corresponding initial responses in longitudinal and circular muscle respectively. These served as time-matched controls for comparison with responses evoked by $[K^+]_O$ (30 mM & 120 mM) in the presence of various L-type $Ca^{2+}$ antagonists (see FIGS. 3-5). In other experiments, the effects of Bay K 8644 (1.0 μM) were examined. In the presence of Bay K 8644 (1.0 μM), longitudinal and circular muscle contractions to $K^+]_O$ (30 & 120 mM) were markedly enhanced, had profiles qualitatively similar to that observed in the presence of FPL 64176 (1.0 μM) as described above (see top traces in FIGS. 6A & 6B) but with one notable difference. After the first series of contractions to high $[K^+]_O$ in the presence of Bay K 8644 (1.0 μM), the second exposures to $[K^+]_O$ (30 & 120 mM) evoked contractions that measured ~92% and 86-92% of the corresponding initial responses in longitudinal and circular muscle (n=4 respectively). This contrasts with the markedly enhanced contractions produced by repeated exposure to high $[K^+]_O$ (30 & 120 mM) in the presence of FPL 64176 (1.0 μM) as described above.

Effects of L-Type $Ca^{2+}$ Antagonists on Contractions Evoked by High $[K^+]_O$ in the Presence of FPL 64176

Longitudinal muscle contractions evoked by $[K^+]_O$ (30 mM & 120 mM) in the presence of FPL 64176 (1.0 μM) were inhibited by the conventional L-type $Ca^{2+}$ antagonists (nifedipine, 0.1 & 1 μM and methoxyverapamil, 0.1 & 1 μM) and by various diphenylalkylamines (pimozide, 1 & 10 μM; fendiline, 1 & 10 μM and prenylamine, 1 & 10 μM). FIG. 3 illustrates the protocol used in these experiments and shows the effects of the diphenylalkylamine, fendiline (10 μM) and the dihyropyridine, nifedipine (0.1 μM). The inhibitory action of diphenylalkylamines was use-dependent and required 100-fold higher concentration than the conventional L-type $Ca^{2+}$ antagonist. The use-dependent inhibition of longitudinal muscle contractions to $[K^+]_O$ (120 mM) by fendiline (10 μM) in comparison to inhibition by nifedipine (0.1 μM) are summarised in FIGS. 3 (B & D).

Circular muscle contractions evoked by $[K^+]_O$ (30 mM & 120 mM) in the presence of FPL 64176 (1.0 μM) were also inhibited in a use-dependent manner by the various diphenylalkylamines as shown in FIG. 4 for fendiline (10 μM) in comparison to nifedipine (0.1 μM). However, in contrast to the effects in longitudinal muscle, diphenylalkylamines produced a peculiar inhibitory action against circular muscle contractions evoked by $[K^+]_O$ (30 mM). The drugs reliably reduced the tonic part of the contractions to $[K^+]_O$ (30 mM) but the superimposed rhythmic contractility was either unchanged or increased in amplitude. This is shown for fendiline (10 μM) in FIG. 4A, in which the overall contraction (rhythmic contractility and tonic response) to $[K^+]_O$ (30 mM) was reduced by 35% compared to time matched controls (also see FIG. 5).

The comparative effects of various diphenylalkylamines and the conventional L-type $Ca^{2+}$ antagonists (nifedipine and methoxyverapamil) against longitudinal and circular muscle contractions evoked by $[K^+]_O$ (30 mM) in the presence of FPL 64176 (1.0 µM) are summarised in FIG. 5. Longitudinal and circular muscle contractions to $[K^+]_O$ (30 mM) were inhibited comparably either by nifedipine (0.1 µM) or methoxyverapamil (1.0 µM) and also by the diphenylalkylamine, pimozide (10 µM) although less potently than the conventional L-type $Ca^{2+}$ antagonists. Other diphenylalkylamines, such as fendiline (10 µM) or prenylamine (10 µM) were significantly ($P<0.05$) more effective against longitudinal compared to circular muscle contractions (respectively 77-82% and 35-38% inhibition compared to time-matched controls). Flunarizine (10 µM) produced a more variable inhibitory action than other diphenylalkylamines and reduced longitudinal and circular contractions to $[K^+]_O$ (30 mM) in the presence of FPL 64176 (1.0 µM) by 20-30% (FIG. 5).

Contractions evoked by higher $[K^+]_O$ (120 mM in the presence of FPL 64176) in longitudinal and circular muscle were also inhibited as described above; differentially by the diphenylalkylamines, prenylamine (10 µM) or fendiline (10 µM) but comparably by nifedipine (0.1 µM, see FIGS. 4 & 3) or methoxyverapamil (1.0 µM, 93-98% inhibition in both muscle types, not shown) and by the diphenylalkylamines, pimozide (10 µM, respectively 71% & 55% inhibition in longitudinal and circular muscle, not shown) or flunarizine (10 µM, 40-44% inhibition in both muscle types, not shown).

Figure 6A:
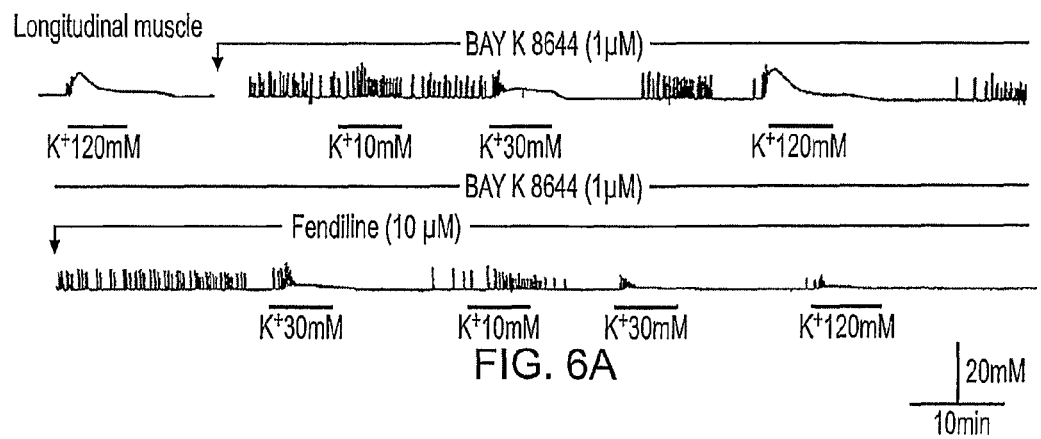
Figure 6B:
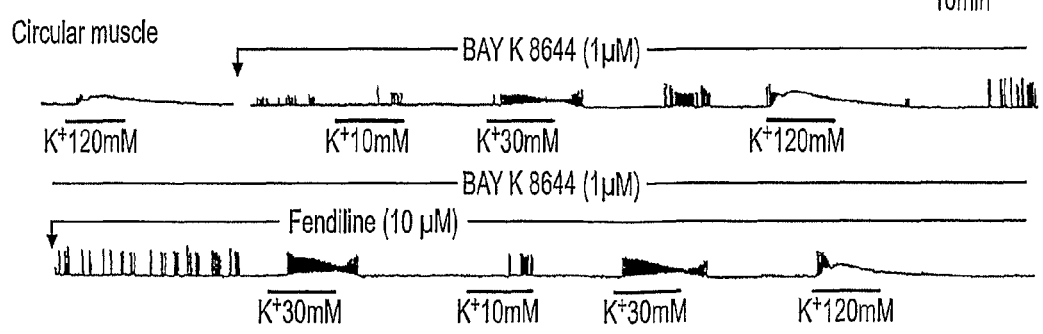

In general, the diphenylalkylamines were less effective than the conventional L-type $Ca^{2+}$ antagonists (nifedipine and methoxyverapamil) against the recurrent rhythmic contractility induced in both muscle types during prolonged ($\geq 20$ min) exposure to either FPL 64176 (1 µM) or Bay K 8644 (1 µM) or against the rhythmic contractility evoked by $[K^+]_O$ (10 mM) in the presence of the L-type $Ca^{2+}$ agonists. Inhibition of the recurrent rhythmic contractility by diphenylalkylamines was achieved with relatively high concentrations (10 µM) of the drugs and only after prior (use-dependent) activation of the tissues with $[K^+]_O$ (30 or 120 mM). This is illustrated in FIG. 6 which shows the recurrent contractility during prolonged exposure to Bay K 8644 (1 µM) and the effects of fendiline (10 µM). Longitudinal (FIG. 6A) and circular muscle (FIG. 6B) contractions to $[K^+]_O$ (30 mM & 120 mM) in the presence of Bay K 8644 (1 µM) also displayed differential sensitivity to fendiline (10 µM) as observed with FPL 64176. The diphenylalkylamine was more effective against $[K^+]_O$ (30 mM & 120 mM)-induced contractions of longitudinal (73-80% inhibition relative to time-matched controls) than of circular muscle (0-20% inhibition relative to time-matched controls). In comparison, exposure nifedipine (1 µM) inhibited comparably $[K^+]_O$ (30 mM & 120 mM)-induced contractions of both muscle types (longitudinal & circular muscle, 66-73% inhibition relative to the respective time-matched controls, not shown). It was also observed that inhibition of the actions of Bay K 8644 (1 µM) by nifedipine required concentrations (nifedipine, 1 µM) higher than was effective (0.1 µM) against the actions of FPL 64176 (1 µM). Inhibitory Potencies of Conventional L-Type $Ca^{2+}$ Antagonists, Diphenylalkylamines and Phenothiazines A separate series of experiments was undertaken to quantify the inhibitory potencies of the conventional L-type Cα antagonists and diphenylalkylamines against contractions of longitudinal and circular muscle evoked by high $[K^+]_O$ (120 mM) in the presence of FPL 64176 (1.0 µM). These experiments used a protocol that took account of the use-dependent inhibitory action shown by the drugs (see Methods).

The phenothiazines (thioridazine and its metabolite, sulphoridazine, trifluoperazine and chlorpromazine) were included in these experiments because of earlier findings that thioridazine blocks L-type $Ca^{2+}$ channels but produces a differential inhibition of the contractions in the muscle types of human vas deferens (see Introduction) similar to the effects of some of the diphenylalkylamines described above. Trifluoperazine and chlorpromazine are structurally similar to thioridazine as shown in FIG. 9 and widely used as CaM antagonists. The inhibitory potencies ($IC_{50}$ values) determined for the various drugs against contractions of longitudinal and circular muscle evoked by high $[K^+]_O$ (120 mM) in the presence of FPL 64176 (1.0 µM) are shown in Table 1. The contractions of both muscle types were inhibited comparably and potently with submicromolar $IC_{50}$ values by nifedipine or methoxyverapamil and comparably but less potently with $IC_{50}$ values in micromolar range by cinnarizine, pimozide, sulphoridazine, chlorpromazine or trifluoperazine. In contrast, fendiline, prenylamine and thioridazine ($IC_{50}$ values in micromolar range) were significantly more potent against longitudinal than circular muscle contractions.

TABLE 1

$IC_{50}$ values of L-type $Ca^{2+}$-antagonists, diphenylalkylamines and phenothiazines

| Drugs | Longitudinal muscle | Circular muscle |
| --- | --- | --- |
| Nifedipine | 2.16 ± 0.8 nM | 2.19 ± 0.5 nM |
|  | (n = 4) | (n = 3) |
| Methoxyverapamil | 16.0 ± 0.9 nM | 18.1 ± 3.8 nM |
|  | (n = 4) | (n = 3) |
| Mibefradil | 1.1 ± 0.2 µM | 2.4 ± 0.9 µM |
|  | (n = 5) | (n = 5) |
| Cinnarizine | 11.4 ± 3.3 µM | 18.5 ± 5.7 µM |
|  | (n = 4)[5] | (n = 3)[6] |
| Flunarizine | >30 µM | >30 µM |
|  | (n = 4) | (n = 4) |
| Fendiline | 3.8 ± 0.9 µM* | 17.4 ± 5.8 µM* |
|  | (n = 6) | (n = 4)[6] |
| Prenylamine | 3.1 ± 0.3 µM* | 8.4 ± 1.8 µM* |
|  | (n = 7) | (n = 7) |
| Pimozide | 4.4 ± 0.6 µM | 8.9 ± 3.1 µM |
|  | (n = 4) | (n = 5) |
| Thioridazine | 7.9 ± 2.3 µM* | 22.3 ± 3.3 µM* |
|  | (n = 6)[8] | (n = 4)[8] |
| Sulphoridazine | 15.9 ± 2.9 µM | 14.1 ± 4.9 µM |
|  | (n = 4) | (n = 4) |
| Chlorpromazine | 12.4 ± 2.9 µM | 18.3 ± 6.0 µM |
|  | (n = 4)[5] | (n = 4)[6] |
| Trifluoperazine | 20.7 ± 5.4 µM | 10.2 ± 3.0 µM |
|  | (n = 4)[6] | (n = 3)[6] |

Inhibition of contractions in longitudinal and circular muscle of human vas deferens evoked by $K^+$ (120 mM) in the presence of the L-type $Ca^{2+}$-agonist, FPL 64176 (1 µM) Asterisks denote significantly different ($P < 0.05$) $IC_{50}$ values. Data are means ± S.E.M. (n) indicates the number of tissues at which drug action in the dose range (1-30 µM) resulted in ≥50% inhibition of longitudinal or circular muscle contractions. Numbers in square brackets indicate the total number of tissues used in experiments with each drug.

Discussion

The results of the present study show that longitudinal and circular muscle of human vas deferens were quiescent to FPL 64176 or Bay K 8644 ($\leq 3$ µM, ~10 min) but higher concentrations of the L-type $Ca^{2+}$ agonists, evoked intermittent rhythmic contractile activity. Prolonged exposure to the drugs (1 µM, ≥25 min) also produced either no response or recurrent rhythmic contractility in both muscle types even in moderately depolarizing ($[K^+]_o$ 10 mM) medium. These findings suggest low basal activity of L-type VOCs in both muscle types. Although there are drawbacks in using contractility as an indication of L-type Ca$^{2+}$ channel function, the finding that the rhythmic contractility evoked by L-type Ca$^{2+}$ agonists that act via different mechanisms [66, 86, 87, 115, 129] were inhibited by different types of conventional L-type Ca$^{2+}$ antagonists (nifedpine or methoxyverapamil) suggests that the responses originate from the activation of L-type VOCs. This is also supported by the finding that stimulation with high [K$^+$]$_O$ (30 mM or 120 mM) in the presence of L-type Ca$^{2+}$ agonists produced markedly enhanced contractions that were inhibited by nifedpine or methoxyverapamil with sub-micromolar IC$_{50}$ values (Table 1) comparable to their published potencies as L-type Ca$^{2+}$ antagonists [45, 108]. However, the depolarization-induced contractions had remarkably different profiles in longitudinal and circular muscle and were differentially inhibited by subsets of diphenylalkylamines and phenothiazines.

The profile of contractions in circular muscle with a predominance of rhythmic activity ([K$^+$]$_O$ 30 mM) and slow time to peak and decline ([K$^+$]$_O$ 120 mM) is clearly different from the pattern in longitudinal muscle which exhibits a more tonic response([K$^+$]$_O$ 30 mM) and rapid time to peak and decline ([K$^+$]$_O$ 120 mM). Given that the contractions in both muscle types were blocked by nifedipine or by methoxyverapamil; indicating their dependence mainly on the activation of L-type VOCs, the different contractile profiles suggests that the muscle types differ in mechanisms that modulate activity of L-type VOCs and in handling of elevated cytosolic Ca$^{2+}$. The mechanisms are presently unclear but may well involve differential modulation of L-type VOCs by Ca$^{2+}$-dependent ancillary currents [e.g. K$^+$ currents, 26, 54, 79, 80]. Electrophysiological studies by Park et al., [82] showed that depolarization of human vas deferens smooth muscle cells evoked oscillatory outward potassium (K$^+$) currents that can be resolved pharmacologically into Ca$^{2+}$-dependent K$^+$ (BK$_{Ca}$) and delayed rectifier K$^+$ (K$_{DR}$) currents. Although it is not clear whether the Ca$^{2+}$-dependent K$^+$ currents were recorded in smooth muscle cells from longitudinal or circular layer, there is evidence that such currents (BK$_{Ca}$ and K$_{DR}$) play different roles in regulating longitudinal and circular muscle contractility in some tissues [25, 111, 112, 118]. The different patterns of contractions in longitudinal and circular muscle may also involve other mechanisms. For example, the L-type Ca$^{2+}$ channels in longitudinal and circular muscle may be associated with different auxiliary subunits [e.g. β-subunits, 21, 88] leading to muscle-type specific modulation of L-type VOC activity [see 52, 100, 120]. It is also possible that the different patterns of contractions originates from muscle-type specific activity of distinct CaM-dependent kinase/enzymes, which can influence smooth muscle contractility by modulating the activity of L-type VOCs [31, 57, 58, 67, 69, 70, 71] or the activity of Ca$^{2+}$-dependent K$^+$ channels [BK$_{Ca}$/K$_{DR}$, 62, 63, 94, 125] or intracellular Ca$^{2+}$ handling (release and resequestration) mechanisms [39, 48, 113, 121, 127]. Further studies are required in order to elucidate the roles and muscle-type specific expression of CaM-dependent enzymes in human vas deferens.

A paradoxical finding is that depolarization-induced contractions of longitudinal compared to circular muscle were more potently inhibited by the diphenylalkylamines, fendiline and prenylamine and by the phenothiazine, thioridazine. In contrast, structurally similar diphenylalkylamines (cinnarizine, flunarizine and pimozide) or phenothiazines (sulphoridazine, chlorpromazine and trifluoperazine) produced comparable inhibition in both muscle types (Table 1). Judging from the absence of differential inhibition by methoxyverapamil or nifedipine, it seems unlikely that activation of longitudinal and circular muscle involves different subtypes/variants of L-type VOCs because such variants exhibit differential sensitivities to dihydropyridine L-type Ca$^{2+}$ antagonists such as nifedipine [65, 72, 123, 124]. The differential inhibitory action by subsets of diphenylalkylamines and phenothiazines is problematic especially as it has been reported that the drugs block L-type VOCs by binding to the same intracellular site as methoxyverapamil [45, 46, 74 but see 42, 59]. The IC$_{50}$ values for diphenylalkylamines and phenothiazines obtained in the present study are higher than their published potencies as L-type Ca$^{2m}$ antagonists [see 45]. The basis for this is unclear but may reflect reports that the drugs are generally less potent than conventional L-type Ca$^{2+}$ antagonists and weakly block the actions of L-type Ca$^{2+}$ agonists [117, 126 also see 104, 106, 107]. Nevertheless, it is noteworthy that the IC$_{50}$ values for cinnarizine, trifluoperazine, chlorpromazine and sulphoridazine are comparable in longitudinal and circular muscle (Table 1) and within the concentration range (≥10 µM) at which these class of drugs inhibit depolarization-induced Ca$^{2+}$ influx [19, 27, 32, 40, 49] and contraction in a number of nonvascular smooth muscles (Hay & Wadsworth 1982; Cortijo et al., 1987; Cejalvo et al., 1993). It is also particularly striking that the IC$_{50}$ values for fendiline, prenylamine, pimozide and thioridazine against circular muscle contractions are within this range. These considerations suggest (i) that the inhibitory effects of diphenylalkylamines and phenothiazines observed in both muscle types involves the blockade of L-type VOCs (also see next paragraph) and (ii) that the greater sensitivity of longitudinal compared to circular muscle contractions to subsets of these drugs (fendiline, prenylamine and thioridazine) originates from additional but unique drug actions in longitudinal muscle. This unique action, which is not shared by other diphenylalkylamines is directed against a muscle type-specific mechanism(s) that contributes more to contractility in longitudinal than in circular muscle.

Diphenylalkylamines and phenothiazines also exhibit pharmacological action as calmodulin (CaM) antagonists [45, 85]. The issue is how inhibition of CaM activity by a subset of these drugs can lead to different effects in longitudinal and circular muscle of human vas deferens. Briefly, smooth muscle contraction relies primarily on Ca$^{2+}$-CaM activation of myosin light chain kinase (MLCK); a kinase dedicated to the phosphorylation of myosin light chain regulatory subunit, which underpins actin-myosin interaction. It seems improbable that inhibition of MLCK activation by a given CaM antagonist would lead to different effects in smooth muscles of the same tissue. Apart from this, studies using skinned smooth muscle and other preparations have reported that diphenylalkylamines and phenothiazines reliably inhibit Ca$^{2+}$-CaM/MLCK activation only at concentrations (≥100 µM) higher than was effective in the present study [32, 33, 34, 64, 93, 105 also see 37]. Ca$^{2+}$-CaM is also involved in Rho A-Rho kinase mediated Ca$^{2+}$-sensitization and smooth muscle contraction [23, 92, 114]. Experiments with the selective inhibitor of Rho kinase, Y 27632 found that the drug produced a comparable inhibition of longitudinal and circular muscle contractions evoked by either noradrenaline or tissue depolarization [12]. Thus, it is unlikely that inhibition of CaM activity at the level of MLCK or Rho kinase underlies the effects of diphenylalkylamines and phenothiazines or the differential action by a subset of the drugs. However, evidence from earlier studies by Zimmer & Hofmann [130, 131] indicate that a number of diphenylalkylamines bind or interact differently with CaM compared to trifluoperazine or chlorpromazine and more potently inhibit CaM activation of distinct CaM-dependent enzymes than of MLCK [44, 51, 91, 110]. The implication is that contractility in longitudinal and circular muscles of human vas deferens may involve the regulatory action of distinct $Ca^{2+}$/CaM-dependent enzyme cascades possibly through muscle-type specific modulation of L-type VOCs, other ion channels or contractile pathways.

In conclusion, the results of this study indicate that longitudinal and circular muscle of human vas deferens exhibit low basal activity of L-type VOCs. However, activation of the $Ca^{2+}$ channels by depolarization leads to different patterns of contractions in longitudinal and circular muscle. The finding that the contractions are blocked by different types of conventional L-type $Ca^{2+}$ antagonists (nifedipine or methoxyverapamil) indicate the involvement of L-type VOCs and suggests that the different patterns of contractility originate from muscle type-specific mechanisms that modulate the activity of L-type VOCs and intracellular handling of $Ca^{2+}$. The results also indicate (i) that inhibition of the contractions by diphenylalkylamines and phenothiazines although less potently than the conventional L-type $Ca^+$ antagonists involves the blockade of L-type VOCs and (ii) that the greater sensitivity of longitudinal muscle contractions to subsets of this class of drugs originates from additional action against a muscle type-specific mechanism or target that contributes more to longitudinal than to circular muscle contractility.

A noteworthy aspect of this study is that muscle-type specific inhibition of $Ca^{2+}$/CaM-dependent enzymes other than MLCK [see 128] may well underlie the hitherto unexplained findings that drugs such as phenoxybenzamine, thioridazine, fendiline and prenylamine (but not their pharmacological counterparts) reliably inhibit longitudinal compared to circular muscle contractions of human vas deferens. These diverse drugs share pharmacological action as CaM antagonists but differ from other well established CaM antagonists (e.g. W-7 and trifluoperazine) in their binding to CaM and activity profile against CaM-dependent enzymes [29, 128]. The clinical relevance of the current study is that it may provide for the first time, a possible pharmacological mechanism underlying the propensity of both phenoxybenzamine and thioridazine (but not their therapeutic counterparts) to inhibit sperm emission [47, 56, 61, 95] by actions in human vas deferens (i.e. without evidence of retrograde ejaculation) and without affecting penile erection, orgasmic sensation, hormonal balance or blood pressure [53, 56]. The differential inhibition of contractility in longitudinal and circular muscle would interfere with the co-ordinated activity that sustains efficient propulsive function of human vas deferens in sperm transport. The dual effect of longitudinal muscle inactivation and unabated circular muscle contraction (lumen closure) would prevent sperm transport and inhibit emission.

EXAMPLE 3

Functional Evaluation of New Compounds in Human Vas Deferens Preparations

Five of the compounds shown in FIG. 10, namely NIBA(2)XC2, NIBA(1)XC1, NIBA(53)XN16, NIBA(6)XN3 and NIBA(14)XN10, which were designed based on comparative functional and structural studies of longitudinal muscle with selected diphenylalkylamines, fendiline, prenylamine and phenothiazine, thioridazine and their structural analogues, which exhibited little or no muscle-type selectivity; (diphenylalkylamines; pimozide, cinnarizine and flunarizine and phenothiazines; sulphoridazine, chlorpromazine and trifluoperazine, see Table 1).

Materials and Methods

Preparation of Tissues

Human vas deferens specimens were obtained after elective vasectomies of healthy fertile men. College ethical approval and the consent of patients were obtained. The specimens were placed in ice-cold Krebs' medium, dissected-free of connective tissue/blood vessels and cut longitudinally into strips (longitudinal muscle preparations; 5-8 mm long & 1 mm wide) or transversely into rings (circular muscle preparations; ~3 mm in length). The longitudinal and circular muscle preparations were then set up for tension recording (resting tension 5-7 mN) in a Perspex chamber superfused at 2 ml per min with Krebs' medium (36° C.) composed of (mM): NaCl, 118.8; $NaHCO_3$, 25; KCl, 4.7; $CaCl_2.2H_2O$, 2.5; $KH_2PO_4$, 1.2; $MgSO_4.7H_2O$, 1.2; glucose, 11.1; ascorbic acid 0.1 and continuously gassed with 95% $O_2$ and 5% $CO_2$. Contractile responses were recorded via a Harvard type force-displacement transducer. The analog signals were digitised using CIO-Das 16/Jr data acquisition software (Amplicon Liveline, Brighton, UK) and re-plotted on a microcomputer.

Evaluation of the New Molecules against Contractions to High Concentrations of Potassium ($[K^+]_o$)

Tissues were equilibrated for 180 min in Krebs' medium containing inhibitors of extraneuronal and neuronal reuptake of noradrenaline, oestradiol (1 μM) and desipramine (0.1 μM) respectively, inhibitors of catechol-O-methyltransferase and monoamine oxidase, tropolone (10 μM) and iproniazid (10 μM) respectively and the β-adrenoceptor blocker, propranolol (1 μM). At the end of the equilibration period, the tissues were stimulated with noradrenaline (100 μM). Subsequently, the tissues were superfused and maintained throughout the experimental period in Krebs' medium containing the $α_1$-adrenoceptor antagonist, prazosin (10 μM), the adrenergic neuron blocker, guanethidine (10 μM,) and tetrodotoxin (0.1 μM). After 40-45 min in this medium the tissues were stimulated with high $[K^+]_O$ (120 mM, Initial response). This was followed by exposure to cumulative concentrations of the new molecules {NIBA(1)XC1, NIBA(14)XN10, NIBA(6)XN3, NIBA(2)XC2, NIBA(53)XN16} or to Krebs' medium containing drug vehicles (time-matched controls). After contact times of 40-60 min at each drug concentration, the tissues were stimulated with high $[K^+]_o$ (120 mM). The resulting contractions were measured using computer software developed in-house to measure the total response (i.e. rhythmic activity plus tonic contraction). Contractions obtained in the presence of the new drug molecules were expressed as a percentage of the initial contraction evoked by high $[K^+]_o$ (120 mM) before exposure to the drugs. Contractions obtained in experiments carried out in drug-free/vehicle medium were expressed in a similar manner and were used to obtain time-matched controls. Percentage inhibition each concentration of the new molecules was calculated with respect to corresponding time-matched controls and concentrations producing 50% reduction of the contractions ($IC_{50}$) were determined by linear regression.

Drugs

Drugs used were as follows: noradrenaline tartrate (Winthrop Laboratories, Guildford, Surrey, UK), propranolol hydrochloride (ICI, Macclesfield, Cheshire, UK). Prazosin hydrochloride from Tocris (Northpoint, Bristol, UK). Desipramine hydrochloride, 1713-oestradiol, dimethyl sulfoxide (DMSO), guanethidine monosulphate, tetrodotoxin (TTX), iproniazid hydrochloride, tropolone, and ascorbic acid all from Sigma (Poole, UK). Stock solutions of desipramine, tropolone, iproniazid, TTX, guanethidine, were prepared in distilled water and the new molecules in DMSO. Aliquots added to drug perfusates or vehicle controls had a final DMSO concentration of less than 0.01%. Solutions containing high concentrations of potassium were prepared by isosmotic replacement of NaCl with KCl.

Results and Discussion

Effects of the New Drug Molecules on High $[K^+]_O$-Induced Contractions

Table 2 shows the inhibitory potencies ($IC_{50}$ values) of the new drug molecules against contractions evoked by high $[K^+]_O$ in longitudinal and circular muscle of human vas deferens. The new drug molecules {NIBA(1) XC1, NIBA(14) XN10, NIBA(6)XN3 and NIBA(2)XC2} were to different extents, more effective against longitudinal than circular muscle contractions and four of these exhibited improved longitudinal muscle selectivity compared to the parent compounds. Longitudinal muscle selectivity assessed from the ratio of $IC_{50}$ values in circular and longitudinal muscles ranged from 2.69 to 7.01 for the new drug molecules (Table 2) compared to selectivity values of 1.7 to 3.6 for the parent compounds (thioridazine, prenylamine and fendiline) (Table 1).

TABLE 2

Functional inhibitory potencies ($IC_{50}$ values) of new drug molecules in longitudinal and circular muscle of human vas deferens. Preliminary Data.

| New Compounds | Longitudinal muscle | Circular muscle | Selectivity [(C/L)-1] |
|---|---|---|---|
| 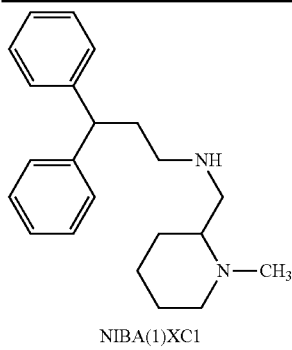 NIBA(1)XC1 | 3.02 µM | 24.2 µM | 7.01 |
| 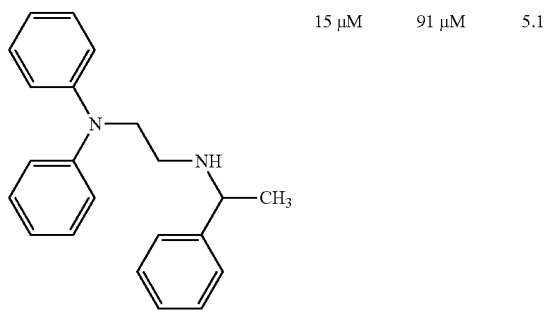 NIBA(14)XN10 | 15 µM | 91 µM | 5.1 |
| 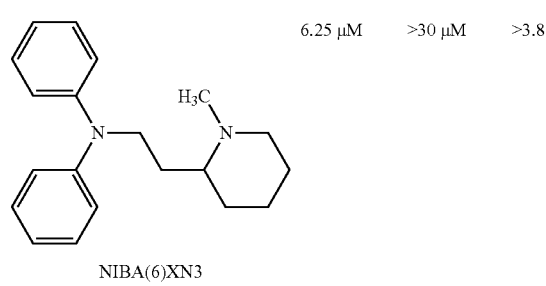 NIBA(6)XN3 | 6.25 µM | >30 µM | >3.8 |

TABLE 2-continued

Functional inhibitory potencies ($IC_{50}$ values) of new drug molecules in longitudinal and circular muscle of human vas deferens. Preliminary Data.

| New Compounds | Longitudinal muscle | Circular muscle | Selectivity [(C/L)-1] |
|---|---|---|---|
| NIBA(2)XC2 | 3.0 µM | 11.07 µM | 2.69 |
| NIBA(53)XN16 | 4.5 µM | 11 µM | 1.4 |

Data are mean values from a small sample study (n=2-3) of the new drugs molecules in the dose range (variously 1-00 µM) which resulted in ≥50% inhibition of contractions evoked by $K^+$ (120 mM).

In conclusion, the findings from studies with the new molecules indicate that these compounds have enhanced selective targeting of the muscle types in human vas deferens.

REFERENCES

1. Aitken, R. J., (2002). Immunocontraceptive vaccines for human use. J. Reprod. Immunol. 57, 273-287.
2. Amobi, N. I. B., Smith, I. C. H., 1992. Effects of thioridazine on mechanical responses of the human vas deferens induced by noradrenaline or potassium. J. Reprod. Fertil. 95, 1-10.
3. Amobi, N. I. B., Smith, I. C. H., 1993. The relative importance of extracellular and intracellular calcium in the responses of the human vas deferens to noradrenaline and potassium: a study using $Ca^{2+}$-deprivation and $Ca^{2+}$-antagonists. J. Auton. Pharmacol. 13, 177-192.
4. Amobi, N. I. B., Smith, I. C. H., 1995a. Differential inhibition in the human vas deferens by phenoxybenzamine: A possible mechanism for its contraceptive action. J. Reprod. Fertil. 103, 215-221.
5. Amobi, N. I. B. & Smith I. C. H. 1995b. The human vas deferens: correlation of response pattern to noradrenaline and histological structure. Eur. J. Pharmacol., 273, 25-34.
6. Amobi, N. I. B. & Smith I. C. H. 1991. Paradoxical effects of thioridazine on electromechanical coupling in the human and rat vas deferens. Eur. J. Pharmacol., 192, 343-348.
7. Amobi, N. I. B., Smith, I. C. H., 1998a. Electromechanical coupling in Human vas deferens: Effects of agents that modulate intracellular release of calcium. J. Auton. Pharmacol. 18, 157-165.

8. Amobi, N. I. B., Smith, I. C. H., 1998b. Ryanodine and cyclopiazonic acid sensitive components in human vas deferens contraction to noradrenaline. J. Auton. Pharmacol. 18, 167-176.
9. Amobi, N., Guillebaud, J., Coker, C., Mulvin, D., Smith, I., 1999. Functional characterization of $\alpha_1$-adrenoceptor subtypes in longitudinal & circular muscle of human vas deferens. Eur. J. Pharmacol. 367, 291-298.
10. Amobi, N. I., Guillebaud, J., Kaisary, A. V., Turner, E., Smith, I. C., 2002. Discrimination by SZL49 between contractions evoked by noradrenaline in longitudinal and circular muscle of human vas deferens. Br. J. Pharmacol. 136, 127-135.
11. Amobi, N., Guillebaud, J., Kaisary, A., Llyoyd-Davies, R. W., Turner, E., Smith, I. C. H., 2003. Contractile actions of imidazoline $\alpha$-adrenoceptor agonists and effects of non-competitive $\alpha_1$-adrenoceptor antagonists in human vas deferens. Eur. J. Pharmacol. 462, 169-177.
12. Amobi, N. I., Chung, I-P., Smith, I. C. H., 2004. Effects of Rho-kinase inhibitors in rat and human epididymal vas deferens. J. Physiol. 565, 166P.
13. Amobi, N. I. B., Guillebaud, J., Turner, E. & Smith, I. C. H., 2006. Contractile actions of L-type $Ca^{2+}$-agonists in human vas deferens and effects of diphenylalkylamines, phenothiazines and L-type $Ca^{2+}$-antagonists. (Unpublished).
14. Amobi, N. I. B., Guillebaud, J., Turner, E. & Smith, I. C. H., 2006. Comparative effects of drugs that inhibit calmodulin-dependent kinases/enzymes on contractility of human vas deferens. (Unpublished).
15. Amory, J. K., 2005. Male hormonal contraceptives: current status and future prospects. Trends in Endocrinol. 4, 333-341.
16. Amory, J. K., Bremner, W. J., 2001. Endocrine regulation of testicular function in men: Implication for contraceptive development. Mol. Cell. Endocrinol. 186, 205-209.
17. Amory, J K, and W J Bremner 2000. "Newer agents for hormonal contraception in the male." Trends in Endocrinology and Metabolism 11, 61-66.
18. Anderson, R. A., Baird, D. T., 2002. Male contraception. Endocr. Rev. 23, 735-762.
19. Asano, M., Hidaka, H.1984. Biopharmacological properties of naphthalenesulfonamides as potent calcmodulin antagonists. In: Cheung, W. Y. (Ed.), Calcium and cell function. Volume V, Academic Press, London, Chapt. 5, pp. 123-164.
20. Batra, S. K. 1974. Sperm transport through the vas deferens: Review of hypothesis and suggestions for a quantitative model. Fert. & Ster., 25, 186-187.
21. Bielefeldt, K., 1999. Molecular diversity of voltage-sensitive calcium channels in smooth muscle cells. J. Lab. Clin. Med. 133, 469-477.
22. Brock, G. B. & Lue, T. F. 1993. Drug-induced male sexual dysfunction. Drug Safety, 8, 414-426.
23. Brozovich, F. V., 2003. Rho signaling: agonist stimulation and depolarization come together. Circ. Res. 93, 481-483.
24. Caldirola, P., Monteil, A., Zandberg, P., Mannhold, R., Timmerman, H., 1997. In vitro and in vivo characterisation of a calcium modulator of the diphenylalkylamine type with selective coronary dilatory properties. Arzneimittelforschung, 47, 1211-1218.
25. Carl, A., Bayguinov, O., Shuttleworth, C. W., Ward, S. M., Sanders, K. M., 1995. Role of Ca(2+)-activated $K^+$ channels in electrical activity of longitudinal and circular muscle layers of canine colon. Am. J. Physiol. 268(3 Pt 1), C619-C627.
26. Carl, A., Lee, H. K., Sanders, K. M., 1996. Regulation of ion channels in smooth muscles by calcium. Am. J. Physiol. 271(1 Pt 1), C9-C34.
27. Cejalvo, D., Calvo, M. A., Lloris, J. M., Cortijo, J., Morcillo, E. J., 1993. Effects of $Ca^{2+}$ channel antagonists in guinea-pig normal and skinned gall bladder. Eur. J. Pharmacol. 234, 23-28.
28. Cheng, C. Y., Mruk, D., Silvestrini, B., Bonanomi, M., Wong, C. H., Siu, M. K., Lee, N. P., Lui, W. Y., Mo, M. Y., 2005. AF-2364 [1-(2,4-dichlorobenzyl)-1H-indazole-3-carbohydrazide] is a potential male contraceptive: a review of recent data. Contraception, 72, 251-261.
29. Cimino, M., Weiss, B., 1988. Characteristics of the binding of phenoxybenzamine to calmodulin. Biochem. Pharmacol. 37, 2739-2745.
30. Clein, L. 1962. Thioridazine and Ejaculation. Br. Med. J., 2, 548-549.
31. Clusin, W. T., Anderson, M. E., 1999. Calcium channel blockers: current controversies and basic mechanisms of action. Adv. Pharmacol., 46, 253-296.
32. Cortijo, J., Foster, R. W., Small, R. C. 1987. Differentiation of calcium antagonists with respect to their effects in normal and skinned taenia caeci preparations. J. Pharm. Pharmacol. 39, 283-289.
33. Cortijo, J., Foster, R. W., Small, R. C., Morcillo, E. J., 1990. Calcium antagonist properties of cinnarizine, trifluoperazine and verapamil in guinea-pig normal and skinned trachealis muscle. J. Pharm. Pharmacol. 42, 405-411.
34. Crosby, N. D., Diamond, J., 1980. Effects of phenothiazines on calcium induced contractions of chemically skinned smooth muscle. Proc. West Pharmacol. Soc. 23, 335-338.
35. Delves, P., 2004. How far from a hormone-based contraceptive vaccine? J. Reprod. Immunol. 62, 6978.
36. Delves, P. J., Lund, T., Roitt, I. M., 2002. Antifertility vaccines. Trends Immunol. 23, 213-219.
37. Douglas, W. W., Nemeth, E. F., 1982. On the calcium receptor activating exocytosis: inhibitory effects of calmodulin-interacting drugs on rat mast cells. J. Physiol. 323, 229-244.
38. Dunn, P. M. 2000. Purinergic receptors and the male contraceptive pill. Curr. Biol., 10, R305-R307.
39. Dyer, J. L., Mobasheri, H., Lea, E. J., Dawson, A. P., Michelangeli, F., 2003. Differential effect of PKA on the $Ca^{2+}$ release kinetics of the type I and III $InsP_3$ receptors. Biochem. Biophys. Res. Commun. 302, 121-126.
40. Flaim, S. F., Brannan, M. D., Swigart, S. C., Gleason, M. M., Muschek, L. D., 1985. Neuroleptic drugs attenuate calcium influx and tension development in rabbit thoracic aorta: effects of pimozide, penfluridol, chlorpromazine, and haloperidol. Proc. Natl. Acad. Sci. U.S.A. 82, 1237-1241.
41. Fovaeus, M., Andersson, K. E., Hedlund, H., 1987. Calcium channel blockade and contractile responses in the isolated human vas deferens. J. Urol. 138, 654-658.
42. Galizzi, J. P., Fosset, M., Romey, G., Laduron, P., Lazdunski, M., 1986. Neuroleptics of the diphenylbutylpiperidine series are potent calcium channel inhibitors. Proc. Natl. Acad. Sci. U.S.A. 83, 7513-7517.
43. Garbers, D. L., 2001. Ion channels: Swimming with sperm. Nature, 413, 579-582.
44. Gigl, G., Hartweg, D., Sanchez-Delgado, E., Metz, G., Gietzen, K., 1987. Calmodulin antagonism: a pharmacological approach for the inhibition of mediator release from mast cells. Cell Calcium 8, 327-344.

45. Godfraind, T., Miller, R., Wibo, M., 1986. Calcium antagonism and calcium entry blockade. Pharmacol. Rev. 38, 321-416.
46. Gould, R. J., Murphy, K. M., Reynolds, I J., Snyder, S. H., 1984. Calcium channel blockade: possible explanation for thioridazine's peripheral side effects. Am. J. Psychiatry. 141, 352-357.
47. Greenberg, H. R., Carrillo, C., 1968. Thioridazine-induced inhibition of masturbatory ejaculation in an adolescent. Am. J. Psychiatry. 124, 991-993.
48. Grover A. K., Xu, A., Samson, S. E., Narayanan, N., 1996. Sarcoplasmic reticulum $Ca^{2+}$ pump in pig coronary artery smooth muscle is regulated by a novel pathway. Am. J. Physiol. Cell Physiol. 271, C181-C187.
49. Hay, D. W., Wadsworth, R. M., 1982. Effects of some organic calcium antagonists and other procedures affecting $Ca^{2+}$ Translocation on KCl-induced contractions in the rat vas deferens. Br. J. Pharmacol. 76, 103-113.
50. Heller. J., 1961. Another case of inhibition of ejaculation as a side-effect of Mellaril. Am. J. Psychiat., 118, 173.
51. Hidaka, H., Yamaki, T., Naka, M., Tanaka, T., Hayashi, H., Kobayashi, R., 1980. Calcium-regulated modulator protein interacting agents inhibit smooth muscle calcium-stimulated protein kinase and ATPase. Mol. Pharmacol. 17, 66-72.
52. Hohaus, A., Poteser, M., Romanin, C., Klugbauer, N., Hofmann, F., Morano, I., Haase, H., Groschner, K., 2000. Modulation of the smooth-muscle L-type $Ca^{2+}$ channel alpha1 subunit (alpha1C-b) by the beta2a subunit: a peptide which inhibits binding of beta to the I-II linker of alpha1 induces functional uncoupling. Biochem. J. 348, 657-665.
53. Homonnai, Z. T., Shilon, M., Paz, G. F., 1984. Phenoxybenzamine: an effective male contraceptive pill. Contraception 29, 479-491.
54. Imaizumi, Y., Torii, Y., Ohi, Y., Nagano, N., Atsuki, K., Yamamura, H., Muraki, K., Watanabe, M., Bolton, T. B., 1998. $Ca^{2+}$ images and $K^+$ current during depolarization in smooth muscle cells of the guinea-pig vas deferens and urinary bladder. J. Physiol. 510, 705-719.
55. Kedia, K. & Markland, C., 1975. The effects of pharmacological agents on ejaculation. J. Urol., 114, 569-572.
56. Kedia, K. R., Persky, L., 1981. Effect of phenoxybenzamine (dibenzyline) on sexual function in man. Urology, 18, 620-621.
57. Keef, K. D., Hume, J. R., Zhong, J., 2001. Regulation of cardiac and smooth muscle Ca(2+) channels (Ca(V)1.2a,b) by protein kinases. Am. J. Physiol. Cell Physiol. 281, C1743-C1756.
58. Kimura, M., Osanai, T., Okumura, K., Suga, S., Kanno, T., Kamimura, N., Horiba, N., Wakui, M., 2000. Involvement of phosphorylation of beta-subunit in cAMP-dependent activation of L-type Ca2+ channel in aortic smooth muscle-derived A7r5 cells. Cell Signal. 12, 63-70.
59. King, V. F., Garcia, M. L., Shevell, J. L., Slaughter, R. S., Kaczorowski, G. J., Substituted diphenylbutylpiperidines bind to a unique high affinity site on the L-type calcium channel. Evidence for a fourth site in the cardiac calcium entry blocker receptor complex. J. Biol. Chem. 264, 5633-5641.
60. Kingsland, J., 2004. Sperm warfare. New Scientist, 181 (#2429), 38-41.
61. Kotin, J., Wilbert, D. E., Verburg, D., Soldinger, S. M., 1976. Thioridazine and sexual dysfunction. Am. J. Psychiatry. 133, 82-85.
62. Koh, S. D., Sanders, K. M., Carl, A., 1996. Regulation of smooth muscle delayed rectifier $K^+$ channels by protein kinase A. Pflugers Arch. 432, 401-412.
63. Koh, S. D., Perrino, B. A., Hatton, W. J., Kenyon, J. L., Sanders, K. M., 1999. Novel regulation of the A-type $K^+$ current in murine proximal colon by calcium-calmodulin-dependent protein kinase II. J. Physiol. 517, 75-84.
64. Kreye, V. A., Ruegg, J. C., Hofmann, F., 1983. Effect of calcium-antagonist and calmodulin-antagonist drugs on calmodulin-dependent contractions of chemically skinned vascular smooth muscle from rabbit renal arteries. Naunyn Schmiedebergs Arch. Pharmacol. 323, 85-89.
65. Lacinova, L., Klugbauer, N., Hofmann, F., 2000. State- and isoform-dependent interaction of isradipine with the alpha1C L-type calcium channel. Pflugers Arch. 440, 50-60.
66. Lauven, M., Handrock, R., Muller, A., Hofmann, F., Herzig, S., 1999. Interaction of three structurally distinct $Ca^{2+}$ channel activators with single L-type $Ca^{2+}$ channels. Naunyn Schmiedebergs Arch. Pharmacol. 360, 122-128.
67. Liu, H., Xiong, Z., Sperelakis, N., 1997. Cyclic nucleotides regulate the activity of L-type calcium channels in smooth muscle cells from rat portal vein. J. Mol. Cell. Cardiol. 29, 1411-1421.
68. Maggi, F. M., Bernini, F., Barberi, L., Fantoni, M., Catapano, A. L., 1993. SIM 6080, a new calcium antagonist, reduces aortic atherosclerosis in cholesterol-fed rabbits. Pharmacol. Res. 28, 219-227.
69. McCarron, J. G., McGeown, J. G., Reardon, S., Ikebe, M., Fay, F. S., Walsh, J. V. Jr. 1992. Calcium-dependent enhancement of calcium current in smooth muscle by calmodulin-dependent protein kinase II. Nature 357, 74-77.
70. McCarron, J. G., McGeown, J. G., Walsh, J. V. Jr., Fay, F. S., 1997. Modulation of high- and low-voltage-activated calcium currents in smooth muscle by calcium. Am. J. Physiol. 273, C883-C892.
71. McDonald, T. F., Pelzer, S., Trautwein, W., Pelzer, D. J., 1994. Regulation and modulation of calcium channels in cardiac, skeletal, and smooth muscle cells. Physiol. Rev. 74, 365-507.
72. Morel, N., Buryi, V., Feron, O., Gomez, J. P., Christen, M. O., Godfraind, T., 1998. The action of calcium channel blockers on recombinant L-type calcium channel alpha1-subunits. Br. J. Pharmacol. 125, 1005-1012.
73. Mulryan, K., Gitterman, D. P., Lewis, C. J., Vial, C., Leckie, B. J., Cobb, A. L., Brown, J. E., Conley, E. C., Buell. G., Pritchard, C. A. & Evans, R. J., 2000. Reduced vas deferens contraction and male infertility in mice lacking P2X1 receptors. Nature, 403, 86-89.
74. Murphy, K. M., Gould, R. J., Largent, B. L., Snyder, S. H., 1983. A unitary mechanism of calcium antagonist drug action. Proc. Natl. Acad. Sci. U.S.A. 80, 860-864.
75. Mousavizadeh, K., Ghafourifar, P., Sadeghi-Nejad, H., 2002. Calcium channel blocking activity of thioridazine, clomipramine and fluoxetine in isolated rat vas deferens: a relative potency measurement study. J. Urol. 168, 2716-2719.
76. Nakanishi, H., Matsuoka, I., Ono, T., Yoshida, H., Uchibori, T., Kogi, K., 1996. Effect of a prenylamine analog (MG8926) on spontaneous action potentials in isolated rabbit sinoatrial node. Fukushima J. Med. Sci. 42, 1-10.
77. Nawrath, H., Klein, G., Rupp, J., Wegener, J. W., Shainberg, A., 1998. Open state block by fendiline of L-type Ca++ channels in ventricular myocytes from rat heart. J. Pharmacol. Exp. Ther. 285, 546-552.

78. Naz, R. K., Gupta, S. K., Gupta, J. C., Vyas, H. K., Talwar, A. G., 2005. Recent advances in contraceptive vaccine development. Hum Reprod. 20, 3271-3283.
79. Nelson, M. T., Quayle, J. M., 1995. Physiological roles and properties of potassium channels in arterial smooth muscle. Am. J. Physiol. 268(4 Pt 1), C799-C822.
80. Ohya, S., Yamamura, H., Muraki, K., Watanabe, M., Imaizumi, Y., 2001. Comparative study of the molecular and functional expression of L-type Ca2+ channels and large-conductance, Ca2+-activated K+ channels in rabbit aorta and vas deferens smooth muscle. Pflugers Arch. 441, 611-620.
81. Orosz, F., Telegdi, M., Liliom, K., Solti, M., Korbonits, D., Ovadi, J., 1990. Dissimilar mechanisms of action of anticalmodulin drugs: quantitative analysis. Mol. Pharmacol. 38, 910-916.
82. Park, S. Y., Lee, M. Y., Keum, E. M., Myung, S. C., Kim, S. C., 2004. Ionic currents in single smooth muscle cells of the human vas deferens. J. Urol. 172, 628-633.
83. Peroutka, S. J., Synder, S. H., 1980. Relationship of neuroleptic drug effects at brain dopamine, serotonin, alpha-adrenergic, and histamine receptors to clinical potency. Am. J. Psychiatry. 137, 1518-1522.
84. Pollack, M. H., Reiter, S., Hammerness, P., 1992. Genitourinary and sexual adverse effects of psychotropic medication. Int. J. Psychiatry Med. 22, 305-327.
85. Prozialeck, W. C., Weiss, B., 1982. Inhibition of calmodulin by phenothiazines and related drugs: structure-activity relationships. J. Pharmacol. Exp. Ther. 222, 509-516.
86. Rampe, D. Dage, R. C., 1992. Functional interactions between two $Ca^{2+}$ channel activators, (S)-Bay K 8644 and FPL 64176, in smooth muscle. Mol. Pharmacol. 41, 599-602.
87. Rampe, D., Anderson, B., Rapien-Pryor, V., Li, T., Dage, R. C., 1993. Comparison of the in vitro and in vivo cardiovascular effects of two structurally distinct $Ca^{++}$ channel activators, BAY K 8644 and FPL 64176. J. Pharmacol. Exp. Ther. 265, 1125-1130.
88. Reimer, D., Huber, I. G., Garcia, M. L., Haase, H., Striessnig, J., 2000. beta subunit heterogeneity of L-type $Ca^{2+}$ channels in smooth muscle tissues. FEBS Lett. 467, 65-69.
89. Ren, D., Navarro, B., Perez, G., Jackson, A. C., Hsu, S., Shi, Q., Tilly, J. L., Clapham. D. E., 2001. A sperm ion channel required for sperm motility and male fertility. Nature. 413, 603-609.
90. Robaire, B., 2003. Advancing towards a male contraceptive: a novel approach from an unexpected direction. Trends in Pharmacol. Sci. 24, 326-328.
91. Roufogalis, B. D., 1982. Specificity of trifluoperazine and related phenothiazines for calcium-binding proteins. In: Cheung, W. Y. (Ed.), Calcium and cell function. Volume III, Academic Press, London, Chapt. 4, pp. 129-159.
92. Sakurada, S., Takuwa, N., Sugimoto, N., Wang, Y., Seto, M., Sasaki, Y., Takuwa, Y., 2003. $Ca^{2+}$-dependent activation of Rho and Rho kinase in membrane depolarization-induced and receptor stimulation-induced vascular smooth muscle contraction. Circ. Res. 93, 548-556.
93. Schachtele, C., Wagner, B., Rudolph, C., 1989. Effect of $Ca^{2+}$ entry blockers on myosin light-chain kinase and protein kinase C. Eur. J. Pharmacol. 163, 151-155.
94. Schubert, R., Nelson, M. T., 2001. Protein kinases: tuners of the $BK_{Ca}$ channel in smooth muscle. Trends Pharmacol. Sci. 22, 505-512.
95. Segraves, R. T., 1982. Male sexual dysfunction and psychoactive drug use: review of a common relationship. Postgrad. Med. 71, 227-33.
96. Shader, R. I. & Grinspoon, L., 1967. Schizophrenia, oligospermia and the phenothiazines. Dis. Nerv. Syst., 28, 240-244.
97. Shader, R. I. 1964. Sexual dysfunction associated with thioridazine hydrochloride. JAMA, 188, 1007-1009.
98. Shi, Y. L., Bai, J. P., Wang, W. P., 2003. Ion-channels in human sperm membrane and contraceptive mechanisms of male antifertility compounds derived from Chinese traditional medicine. Acta Pharmacol Sin., 24, 22-30.
99. Shilon, M., Paz, G. F. & Homonnai, Z. T., 1984. The use of phenoxybenzamine treatment in premature ejaculation. Fertil. Steril., 42, 659-661.
100. Singer, D., Biel, M., Lotan, I., Flockerzi, V., Hofmann, F., Dascal, N., 1991. The roles of the subunits in the function of the calcium channel. Science 253, 1553-1557.
101. Singh, H., 1963. Therapeutic use of thioridazine in premature ejaculation. Am. J. Psychiat., 119, 891.
102. Singh, H., 1961. A case of inhibition of ejaculation as a side effect of Mellaril. Am. J. Psychiat., 117, 1041-1042.
103. Snyder. S. H., Reynolds, I J., 1985. Calcium-antagonist drugs. Receptor interactions that clarify therapeutic effects. N. Engl. J. Med. 313, 995-1002.
104. Spedding, M., 1982. Assessment of "$Ca^{2+}$-antagonist" effects of drugs in $K^+$-depolarized smooth muscle. Differentiation of antagonist subgroups. Naunyn Schmiedebergs Arch. Pharmacol., 318, 234-240.
105. Spedding, M., 1983. Direct inhibitory effects of some 'calcium-antagonists' and trifluoperazine on the contractile proteins in smooth muscle. Br. J. Pharmacol. 79, 225-231.
106. Spedding, M., 1985a. Activators and inactivators of $Ca^{++}$ channels: new perspectives. J. Pharmacol. (Paris), 16, 319-343.
107. Spedding. M., 1985b. Calcium antagonist subgroups. Trends Pharmacol Sci., 6, 109-114.
108. Spedding, M., Paoletti, R., 1992. Classification of calcium channels and the sites of action of drugs modifying channel function. Pharmacol. Rev. 44, 363-376.
109. Su, C. M., Swamy, V. C., Triggle, D. J., 1984. Calcium channel activation in vascular smooth muscle by BAY K 8644. Can. J. Physiol. Pharmacol. 62, 1401-1410.
110. Tanaka, T., Ito, M., Ohmura, T., Hidaka, H., 1985. $Ca^{2+}$-dependent cyclic nucleotide phosphodiesterase is activated by poly(L-aspartic acid). Biochemistry, 24, 5281-5284.
111. Thornbury, K. D., Ward, S. M., Sanders, K. M., 1992a. Outward currents in longitudinal colonic muscle cells contribute to spiking electrical behavior. Am. J. Physiol. 263(1 Pt 1), C237-C245.
112. Thornbury, K. D., Ward, S. M., Sanders, K. M., 1992b. Participation of fast-activating, voltage-dependent K currents in electrical slow waves of colonic circular muscle. Am. J. Physiol. 263(1 Pt 1), C226-C236.
113. Twort, C. H., van Breemen, C., 1988. Cyclic guanosine monophosphate-enhanced sequestration of $Ca^{2+}$ by sarcoplasmic reticulum in vascular smooth muscle. Circ. Res. 62, 961-964.
114. Urban, N. H., Berg, K. M., Ratz, P. H., 2003. $K^+$ depolarization induces RhoA kinase translocation to caveolae and $Ca^{2+}$ sensitization of arterial muscle. Am. J. Physiol. Cell Physiol. 285, C1377-C1385.
115. Usowicz, M. M., Gigg, M., Jones, L. M., Cheung, C. W., Hartley, S. A., 1995. Allosteric interactions at L-type calcium channels between FPL 64176 and the enantiomers of the dihydropyridine Bay K 8644. J. Pharmacol. Exp. Ther. 275, 638-645.
116. van der Spoe,l A. C., Jeyakumar, M., Butters, T. D., Charlton, H. M/, Moore, H. D., Dwek, R. A., Platt, F. M., 2002. Reversible infertility in male mice after oral administration of alkylated imino sugars: a nonhormonal approach to male contraception. Proc. Natl. Acad. Sci. 24, 17173-17178.
117. Vanhoutte, P., Paoletti, R. 1987. The WHO classification of calcium antagonists. Trends Pharmacol. Sci. 8, 4-5.
118. Wade, G. R., Laurier, L. G., Preiksaitis, H. G., Sims, S. M., 1999. Delayed rectifier and $Ca^{2+}$-dependent $K^+$ currents in human esophagus: roles in regulating muscle contraction. Am. J. Physiol. Gastrointest. Liver Physiol. 277, G885-G895.
119. Walden, C. M., Butters, T. D., Dwek, R. A., Platt, F. M., van der Spoel, A. C., 2006. Long-term non-hormonal male contraception in mice using N-butyldeoxynojirimycin. Hum. Reprod. 21, 1309-1315.
120. Walker, D., De Waard, M., 1998. Subunit interaction sites in voltage-dependent Ca2+ channels: role in channel function. Trends Neurosci. 21, 148-154.
121. Wehrens, X. H., Lehnart, S. E., Reiken, S. R., Marks, A. R., 2004. $Ca^{2+}$/calmodulin-dependent protein kinase II phosphorylation regulates the cardiac ryanodine receptor. Circ. Res. 94, e61-e70.
122. Weiss, B., Prozialeck, W., Cimino, M., Barnette, M. S., Wallace, T. L., 1980. Pharmacological regulation of calmodulin. Ann. N.Y. Acad. Sci. 356, 319-345.
123. Welling, A., Kwan, Y. W., Bosse, E., Flockerzi, V., Hofmann, F., Kass, R. S., 1993. Subunit-dependent modulation of recombinant L-type calcium channels. Molecular basis for dihydropyridine tissue selectivity. Circ. Res. 73, 974-980.
124. Welling, A., Ludwig, A., Zimmer, S., Klugbauer, N., Flockerzi, V., Hofmann, F., 1997. Alternatively spliced IS6 segments of the alpha IC gene determine the tissue-specific dihydropyridine sensitivity of cardiac and vascular smooth muscle L-type $Ca^{2+}$ channels. Circ. Res. 81, 526-532.
125. White, R. E., Kryman, J. P., El-Mowafy, A. M., Han, G., Carrier, G. O., 2000. cAMP-dependent vasodilators cross-activate the cGMP-dependent protein kinase to stimulate BK(Ca) channel activity in coronary artery smooth muscle cells. Circ. Res. 86, 897-905.
126. Wilhelm, D. I., Peters, Th., 1985. The influence of calcium and BAY K 8644 on the rat portal vein in the presence of different calcium channel blockers. Naunyn Schmiedebergs Arch Pharmacol. 329, Suppl. R49.
127. Yoshida, Y., Sun, H. T., Cai, J. Q., Imai, S., 1991. Cyclic GMP-dependent protein kinase stimulates the plasma membrane Ca pump ATPase of vascular smooth muscle via phosphorylation of a 240-kDa protein. J. Biol. Chem. 266, 19819-19825.
128. Zhang, S. P., Prozialeck, W. C., Weiss, B., 1990. Differential inhibition of calcium-dependent and calmodulin-dependent enzymes by drug-calmodulin adducts. Mol. Pharmacol. 38, 698-704.
129. Zheng, W., Rampe, D., Triggle, D. J., 1991. Pharmacological, radioligand binding, and electrophysiological characteristics of FPL 64176, a novel nondihydropyridine $Ca^{2+}$ channel activator, in cardiac and vascular preparations. Mol. Pharmacol., 40, 734-741.
130. Zimmer, M., Hofmann, F., 1985. "Calmodulin-antagonists" (CaM-A) reveal differences in the interaction of calmodulin (CaM) with myosin light chain kinase (MLCK) and phosphodiesterase (PDE). Naunyn Schmiedebergs Arch. Pharmacol. 329, R1.
131. Zimmer, M., Hofmann, F., 1987. Differentiation of the drug-binding sites of calmodulin. Eur. J. Biochem. 164, 411-420.

The invention claimed is:

1. A method of reducing sperm emission, or reducing transfer of viruses or microbes found in ejaculatory material of a human male comprising administering an effective amount of a compound having formula I

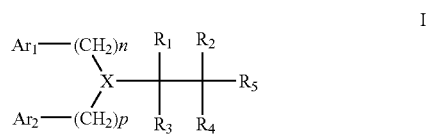

wherein $R_1$, $R_2$, $R_3$ and $R_4$ are independently H;

$R_5$ is selected from the group of structures consisting of:

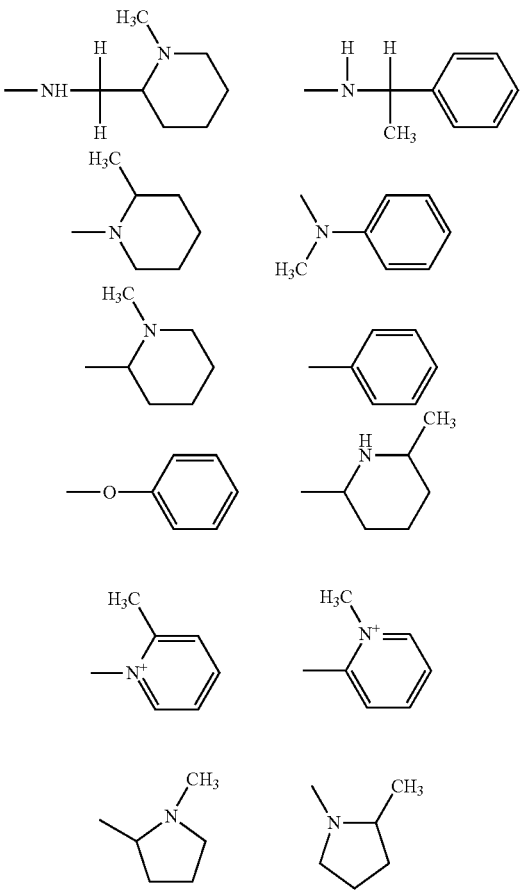

X is CH or N;

n and p are independently whole numbers selected from 0, 1 and 2;

$(CH_2)_n$ and $(CH_2)_p$ are non-substituted; and $Ar_1$ and $Ar_2$ are phenyl or a pharmaceutically acceptable salt.

2. A method according to claim 1, wherein n is 0 or 1.

3. A method according to claim 1, wherein n is 0.

4. A method according to claim 1, wherein p is 0 or 1.

5. A method according to claim 1, wherein p is 0.

6. A method according to claim 1 wherein the compound is selected from the following compounds:
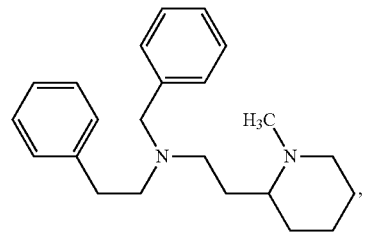
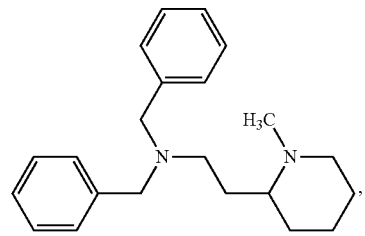
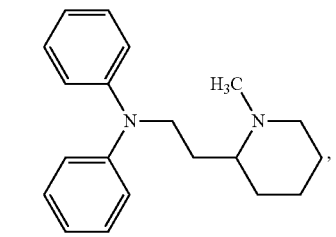
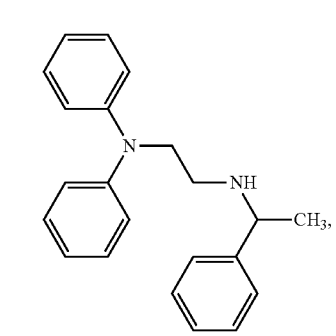
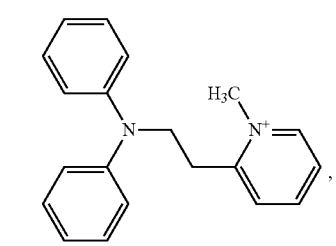
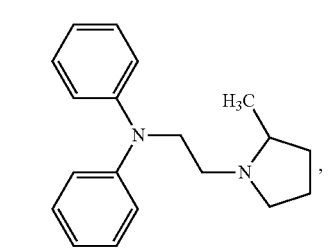
-continued
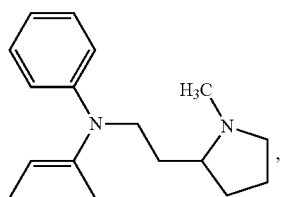
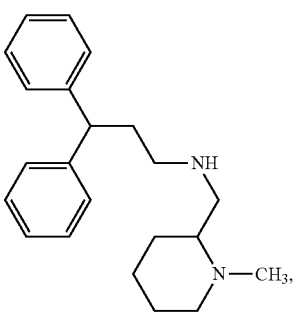
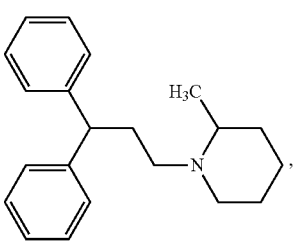
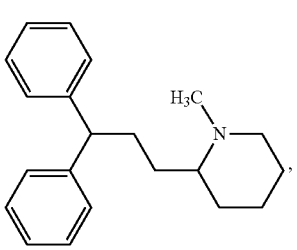
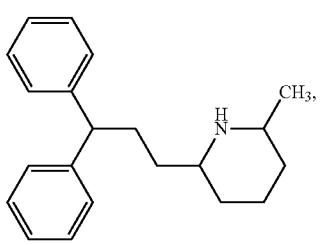
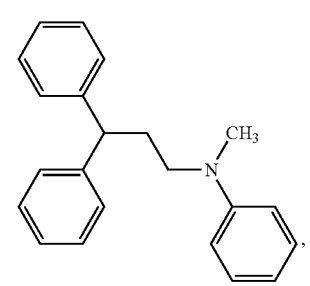

-continued
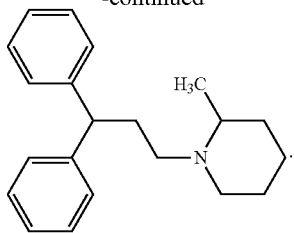
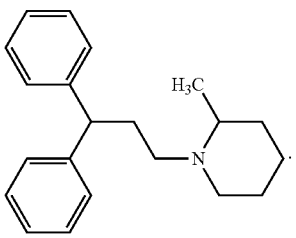
7. A method according to claim 6 wherein the compound is selected from the group consisting of
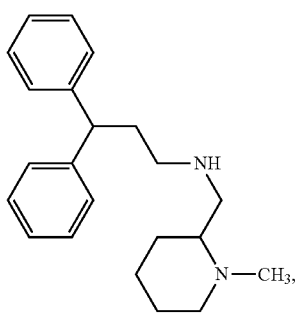
8. A compound which is
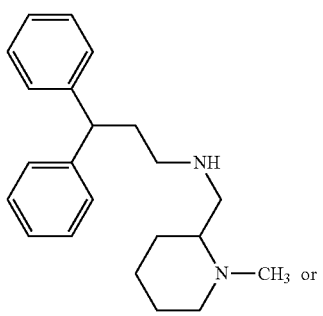
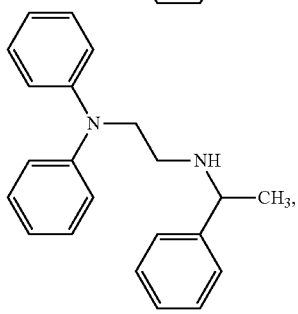
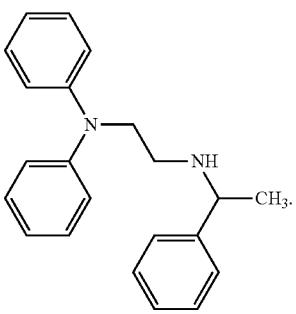
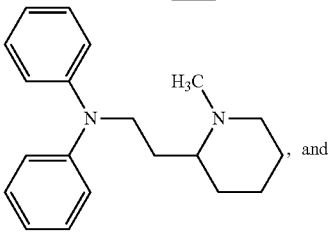, and
* * * * *

UNITED STATES PATENT AND TRADEMARK OFFICE
CERTIFICATE OF CORRECTION

PATENT NO.        : 8,927,579 B2                                Page 1 of 1
APPLICATION NO.   : 12/504287
DATED             : January 6, 2015
INVENTOR(S)       : Nnaemeka Ikechukwu Amobi et al.

It is certified that error appears in the above-identified patent and that said Letters Patent is hereby corrected as shown below:

On the Cover Page, Column 1, (75) Inventors, Line 1
    Please delete "Nnae-Meka" and insert --Nnaemeka--.

On the Cover Page, Column 1, (75) Inventors, Line 2
    Please delete "Christopher" and insert --Ian Christopher--.

On the Cover Page, Column 1, (73) Assignees, Line 1
    Please delete "Nnaemkea" and insert --Nnaemeka--.

On the Cover Page, Column 2, (57) Abstract, Line 1, Formula I
    Please delete "$(CH_2)n$" and insert --$(CH_2)_n$--.

On the Cover Page, Column 2, (57) Abstract, Line 3, Formula I
    Please delete "$(CH_2)p$" and insert --$(CH_2)_p$--.

On Page 2, Column 2, References Cited Other Publications, Line 15
    Please delete "phosphatases" and insert --phosphatase--.

In the claims

In Column 34, Claim 1, Lines 6-10, Formula I
    Please delete "$(CH_2)n$" and insert --$(CH_2)_n$--.

In Column 34, Claim 1, Lines 10-13, Formula I
    Please delete "$(CH_2)p$" and insert --$(CH_2)_p$--.

In Column 37, Claim 7, Line 13
    Please delete "group consisting of" and insert --group consisting of:--.

In Column 38, Claim 8, Line 16
    Please delete "which is" and insert --which is:--.

Signed and Sealed this
Thirteenth Day of October, 2015

Michelle K. Lee
*Director of the United States Patent and Trademark Office*

UNITED STATES PATENT AND TRADEMARK OFFICE
CERTIFICATE OF CORRECTION

PATENT NO. : 8,927,579 B2
APPLICATION NO. : 12/504287
DATED : January 6, 2015
INVENTOR(S) : Amobi et al.

Page 1 of 1

It is certified that error appears in the above-identified patent and that said Letters Patent is hereby corrected as shown below:

Title Page,
Item [73], Assignee, "Nnaemeka" (as corrected to read in the Certificate of Correction issued October 13, 2015) is deleted and patent is returned to its original state with first assignee name in patent to read -- Nnaemkea --.

Signed and Sealed this
Eighth Day of December, 2015

Michelle K. Lee
*Director of the United States Patent and Trademark Office*